(12) United States Patent
Xue et al.

(10) Patent No.: US 6,630,296 B2
(45) Date of Patent: Oct. 7, 2003

(54) MULTIPLEXED ENZYMATIC ASSAYS

(75) Inventors: Qifeng Xue, Freemont, CA (US); Ian Gibbons, Portola Valley, CA (US)

(73) Assignee: Aclara BioSciences, Inc., Mountain View, CA (US)

( * ) Notice: Subject to any disclaimer, the term of this patent is extended or adjusted under 35 U.S.C. 154(b) by 0 days.

(21) Appl. No.: 09/924,692

(22) Filed: Aug. 8, 2001

(65) Prior Publication Data

US 2002/0119500 A1 Aug. 29, 2002

Related U.S. Application Data

(60) Provisional application No. 60/223,832, filed on Aug. 8, 2000.

(51) Int. Cl.[7] ............................ C12Q 1/00; C12Q 1/48; G01N 33/53
(52) U.S. Cl. ............................ 435/4; 435/968; 435/15; 435/966; 435/975; 435/7.1
(58) Field of Search ............................ 435/4, 968, 15, 435/966, 975, 7.1

(56) References Cited

U.S. PATENT DOCUMENTS

| | | | |
|---|---|---|---|
| 5,308,460 A | 5/1994 | Mazid et al. | |
| 5,981,180 A | * 11/1999 | Chandler et al. | 435/6 |
| 6,335,201 B1 | 1/2002 | Allbritton et al. | 436/63 |
| 2002/0037542 A1 | 3/2002 | Allbritton et al. | 435/15 |
| 2002/0127604 A1 | 9/2002 | Allbritton et al. | 702/19 |
| 2002/0142323 A1 | 10/2002 | Allbritton et al. | 436/514 |

FOREIGN PATENT DOCUMENTS

| | | |
|---|---|---|
| WO | WO 01/07910 | 2/2001 |
| WO | 200212547 A1 * | 2/2002 |

OTHER PUBLICATIONS

Lee, C.L., et al., *Nature Biotechnology* 17:759–762, (1999).
McDonald, et al., *Analytical Biochemistry* 268(2):318–329, (1999).
Warrior, et al., *Journal of Biomolecular Screening* 4(3):129–135, (1999).

* cited by examiner

Primary Examiner—Louise N. Leary
(74) Attorney, Agent, or Firm—Perkins Coie LLP

(57) ABSTRACT

A multiplexed enzyme assay method and substrate set for performing the method are disclosed. The method includes performing a plurality of enzyme reactions in the presence of a plurality of enzymes substrates, under conditions effective to convert an enzyme substrate to a corresponding product, where the product of each substrate and the substrate have different separation characteristics from each other and from the other substrates and their corresponding products. After performing the reactions, which may be carried out in separate or combined reactions, the substrates and products in said reactions are separated in a single separation medium. For each separated product and substrate, a separation characteristic effective to identify that product and substrate and a signal related to the amount of the product and substrate is detected. From this, one can determine the amount of substrate converted to the corresponding product in each of the reactions.

25 Claims, 14 Drawing Sheets

MULTIPLEXED ENZYMATIC ASSAYS

This application claims the benefit of U.S. Provisional Application No. 60/223,832 filed Aug. 8, 2000.

TECHNICAL FIELD

The field of this invention is enzyme assays, and in particular, assays involving multiplexed substrates and, optionally multiplexed enzymes.

REFERENCES

Blakesley V. A., Scrimgeour A., Esposito D., Roith D. L., Signaling via the insulin-like growth factor-I receptor: does it differ from insulin receptor signaling?, Cytokine & Growth factor reviews (1996), Vol. 1, 2, pp. 153–159.

Bunemann M., Hosey M. M., G-protein coupled receptor kinases as modulators of G-protein signaling, J. of Physiology (1999), 517, 1, pp.5–23.

Cantley, L. C. et al Signal Transduction in Health and Disease, Advances in Second Messenger and Phosphoprotein Research, Vol. 31, 41–48, 1997.

Cohen, C. B. et al Anal. Biochem. Vol 273, 89–97, 1999.

Pike L. J., Gallis B., Casnellie J. E., Bornstein P., Krebs E. G., Epidermal growth factor stimulates the phosphorylation of synthetic tyrosine-containing peptides by A431 cell membranes,PNAS, USA 79 (1982), pp.1443–1447.

Nanjee, M. N. Clinical Chemistry, Vol. 42(6), 915–926, 1996.

Osorio C. R. et al Dis. Aquat. Organ. Vol. 40(3), 177–183, 2000.

Pike L. J., Kuenzel E. A., Casnellie J. E., Krebs E. G., A comparison of insulin- and epidermal growth factor-stimulated protein kinases from human placenta, J. of Biol. Chem. (1984), 259, 15, pp.9913–9921.

Sasaki N., Rees-Jones R. W., Zick Y., Nissley S. P., Rechler M. M., Characterization of insulin-like growth factor I-stimulated tyrosine kinase activity associated with the β-subunit of type I insulin-like growth factor receptor of rat liver cells, J. of Biol. Chem. (1985), Vol. 260, 17, pp.9793–9804.

White M. F., Kahn C. R., The Insulin Receptor and Tyrosine Phosphorylation, The Enzymes, Vol. XVII, pp.248–310, 1986.

White, M. F. et al The Enzymes Vol. XVII, 247–311, 1986.

Zhou M., Felder S., Rubinstein M., Hurwitz D. R., Ullrich A., Lax I., Schlessinger J., Real time measurements of kinetics of EGF binding to soluble EGF receptor monomers and dimmers support the dimerization model for receptor activation, Biochemistry (1993), 32, 8193–8198.

BACKGROUND OF THE INVENTION

There are numerous situations where one is interested in performing a multiplicity of determinations in a single vessel and being able to individually determine the result of each determination. In order to be able to achieve the individual results, it is necessary that each determination be independent of the other determinations, and that each determination provide a product that can be measured and distinguished from the products of the other determinations.

One of the areas of interest is the effect of a change in environment on a plurality of enzymes. In screening compounds for biological activity, one is interested in the effect of the compound on one or more targets, as well as the effect of the compound on enzymes that are not targets. Therefore, if one can perform a single determination under the same conditions, so as to determine the effect of the compound on a plurality of enzymes, one can not only determine the biological activity of the compound as to targets of interest, but also the specificity of the compound in relation to side effects.

Besides screening compounds for biological activity, there is also an interest in determining the effect of a change in environment on cellular activity, as to specific enzymes. For cancer cells, one would be interested in determining changes in the cellular expression of proteins, the activity of individual enzymes, or an enzyme profile in relation to a compound or course of treatment.

One special class of enzymes for which enzyme multiplexing would be advantageous is cell-surface or intracellular receptors, which represent a significant class of targets for drug screening because the receptors are involved in cell growth and metabolism. Many receptors have enzyme domains, such as the insulin receptor, insulin-like growth factor receptor, epidermal growth factor, and platelet-derived growth factor (White). Some receptors can be coupled to enzyme for assaying the receptors (Bunemann). When a ligand binds to the specific site of a receptor, it typically activates the receptor's enzyme domain. In many cases, the enzyme is protein kinase that can be measured by determination of the rate of phosphorylation of a synthetic peptide. Since many receptors have high affinity to their specific ligands (Pike, 1984, Blakesley, Sasaki), it is possible to develop a method to perform the receptor assay by monitoring their enzyme (kinase) activity. Since only the specifically bound, natural ligand has the potential to activate the enzyme domain, the receptor assay by monitoring its enzyme activity may avoid the non-specific binding issue. This approach can be used for both ligand binding assay and enzyme assay for many receptors, especially for hormones and growth factor receptors.

In screening for compounds that are capable of inhibiting ligand/receptor binding, there are two, and sometimes three, variables that must be screened. The first variable is the test compound itself, e.g., a large number of test compounds derived from a library of potential inhibitors of ligand/ receptor interaction. The second variable is test-compound concentration, relative to the concentration of receptor ligand. The third variable is the effect of the test compound on other enzymes, e.g., other receptor kinases on or in the target cell. Testing for and optimizing the concentration of test compounds, and assaying their effect on other cellular enzymes ultimately requires a large number of assay samples. By combining one or more of the test variables in a multiplexed assay, one could substantially reduce the number of assay that needed to be performed and/or provide an internal control for multiple assays.

SUMMARY OF THE INVENTION

In one aspect, the invention includes a multiplexed enzyme assay method. The method includes performing a plurality of enzyme reactions in the presence of plurality of enzymes substrates in a set of substrates, under conditions effective to convert an enzyme substrate to a corresponding product, where the product of each substrate and the substrate have different separation characteristics from each other and from the other substrates in the set and their corresponding products. After performing the reactions, the products, and preferably also the substrates in the reactions are separated in a single separation medium. For each separated product and substrate, a separation characteristic effective to identify that product and substrate and a signal related to the amount of the product and substrate is detected. From this, the amount of substrate converted to the corresponding product in each of the reactions can be determined.

The separation characteristic of the substrates and products is preferably electrophoretic mobility in an electrophoretic medium under the influence of an electric field, although other separation characteristics, such as behavior when separated by exclusion or ion-exchange chromatography, isoelectric focusing or mass spectroscopy are also contemplated. The substrates and corresponding products may be fluorescent-labeled, where the detecting includes detecting the fluorescent signal from each product when irradiated with a fluorescence-excitation wavelength.

In one general embodiment, the plurality of enzyme reactions are carried out in a single reaction mixture containing a plurality of different enzymes, where each of the enzymes being assayed is effective to convert one of the substrates in the reaction mixture to the corresponding product. The embodiment may be used, for example, to determine the levels of activity of each of a plurality of different enzymes in a cell, under selected cell conditions, where the different enzymes in the reaction mixture are obtained from the cell under such selected cell conditions.

For use in determining changes in the levels of activity of each of a group of enzymes in a cell, in both control and test cell conditions, the performing, separating, detecting, and determining steps are carried out for enzymes obtained from the cells in both the control and test conditions. For example, to determine changes in the levels of activity of each of a group of enzymes in a cell, when the cell is exposed to an agent known or being tested for its ability to inhibit or activate the level of the activity of one or more of the different enzymes, the performing, separating, detecting, and determining steps are carried out for enzymes obtained from the cells before and after exposure to the agent. Exemplary groups of enzymes include receptor-kinase enzymes and cell-signaling pathway enzymes.

In another general embodiment, for use in assaying the effect of one or more agents in inhibiting or stimulating the activity of a selected enzyme, the enzyme reactions are performed in separate reaction mixtures, where each mixture contains (i) one or more enzymes and, (ii) one or more substrates from the set of substrates.

In a more specific embodiment, for use in screening for or evaluating the ability of test compound to affect enzyme activity, the reaction mixtures also contain one or both of (a) one of a plurality of different test agents and/or one of a plurality of different concentrations of a single agent. The reaction mixtures are combined prior to separating the substrates and products of the different reactions.

The different substrates in a set may include (i) an enzyme substrate moiety, (ii) a mobility modifier that imparts to each substrate and its corresponding product in the set, a unique separation characteristic with respect to the separation characteristics of other substrates and corresponding products in the set, and (iii) a reporter moiety that permits detection of a signal from said substrates and products in the set. Where the substrates in a set have an oligopeptide substrate moiety, and the mobility modifier may be (i) non-peptide moieties coupled to the oligopeptide, (ii) one or more amino acid substitutions in said oligopeptide that preserve the substrate moiety but alter the molecular weight and/or charge of the oligopeptide, and (iii) different reporter moieties with different charges and/or molecular weights.

For use in assaying interactions between a receptor enzyme and a ligand known to stimulate the receptor-enzyme activity, the separate enzyme reaction mixtures preferably include (i) the one or more selected enzymes (ii) one or more substrates from the set of substrates, and (iii) one or more different concentrations of the ligand, including, in at least one reaction mixture, a concentration of ligand sufficient to produce optimal activation of the enzyme. One of the reaction mixtures preferably contains no ligand, to provide an enzyme activity level of non-activated enzyme.

The receptor enzyme may be, for example, a receptor-kinase enzyme effective, in an activated state, to phosphorylate an oligopeptide substrate, such as EGFR, where the ligand is EGF, receptor II kinase, where the ligand is insulin, and insulin receptor kinase, where the ligand is insulin. In this receptor-enzyme assay, the substrates in the set include the oligopeptide substrate, and a mobility modifier of the type noted above.

For assaying the ability of one or more test agents to interfere with ligand-activated enzyme activity, at least some of the reaction mixtures contain, in addition to an optimal concentration of ligand, one of a plurality of different test agents. Alternatively, or in addition, at least some of the reaction mixtures contain, in addition to an optimal concentration of ligand, one or more concentrations of at least one test agent.

In another aspect, the invention includes a set of enzyme substrates for performing a multiplexed enzyme assay. The set includes a plurality of enzyme substrates, each having (i) an enzyme substrate moiety at which an enzyme in the assay reacts with the substrate, to convert it to the corresponding product, (ii) a mobility modifier that imparts to each substrate and its corresponding product in the set, a unique separation characteristic with respect to the separation characteristics of other substrates and corresponding products in the set, and (iii) a reporter moiety that permits detection of a signal from said substrates and products in the set. The reporter moiety may be, for example, a fluorescent reporter. The enzyme may be, for example, a kinase from different functional groups of kinases, including cyclic nucleotide-regulated protein kinases, protein kinase C, kinases regulated by $Ca^{2+}$/CaM, cyclin-dependent kinases, ERK/MAP kinases, and protein-tyrosine kinases. The kinase may be a protein kinase enzyme in a signaling pathway, effective to phosphorylate an oligopeptide substrate, such as ERK kinase, S6 kinase, IR kinase, P38 kinase, and AbI kinase. In this enzyme assay, the substrates in the set include the oligopeptide substrate, and a mobility modifier of the type noted above. Other kinases of interest may include, for example, Src kinase, JNK, MAP kinase, cyclin-dependent kinases, P53 kinases, platelet-derived growth factor receptor, epidermal growth factor receptor, and MEK.

For use in a method for assaying one or more enzymes having an oligopeptide substrate, the substrates in a set have an oligopeptide substrate moiety, and the mobility modifier may be (i) non-peptide moieties coupled to the oligopeptide, (ii) one or more amino acid substitutions in the oligopeptide that preserve said substrate moiety but alter the molecular weight and/or charge of the oligopeptide, and (iii) different reporter moieties with different charges and/or molecular weights.

These and other objects and features of the invention will become more fully apparent when the following detailed description of the invention is read in conjunction with the accompanying drawings.

DESCRIPTION OF THE SPECIFIC EMBODIMENTS

Figure 1A:
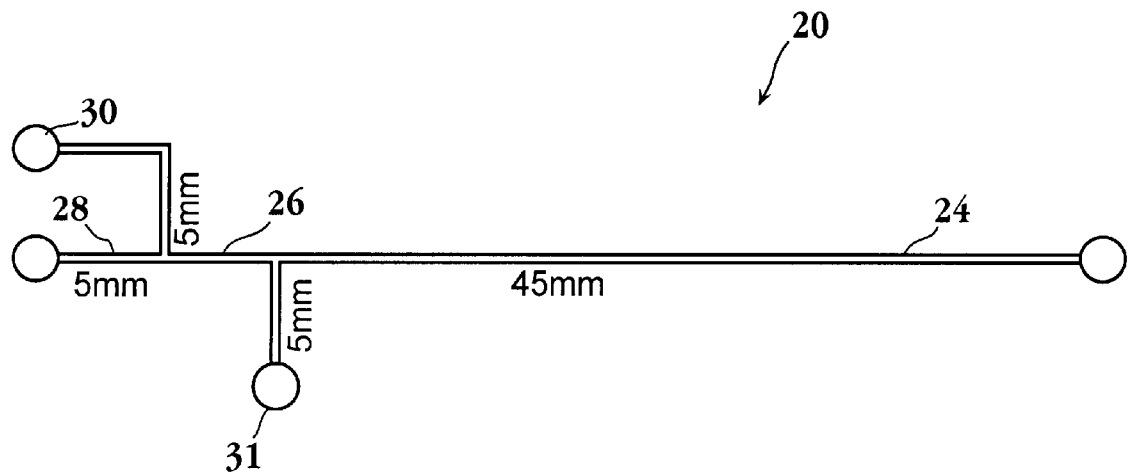
FIGS. 1A and 1B are simplified plan views of microfluidics devices for carrying out electrophoretic separations of multiplexed reactions products, in accordance with the invention.

The present invention is directed to a method for conducting multiplexed enzyme assays, that is, assays in which the results of plural different enzyme assays are monitored or detected in a single detection format. Two general types of multiplexed assays are contemplated. In the first, detailed in Section A, multiple enzymes are assayed in the same reaction mixture in the presence of a plurality or set of different enzyme substrates. Each enzyme is capable of converting one of the substrates to a corresponding product, where the substrates and corresponding products have different, unique separation characteristics that allow the products, and preferably the substrates, to be separated from one another in a single separation medium.

In a second general assay type, detailed in Section B, a plurality of enzyme reactions is carried out separately, e.g., in parallel. The separate reactions may contain one or more of the same or different enzymes, one or more of the same or different enzyme inhibitors or activators, and/or different concentrations of inhibitors, activators, or substrates. As above, each reaction mixture contains one or more substrates capable of being converted to an associated product, where the substrates and corresponding products have different, unique separation characteristics, as above. In one exemplary embodiment, the different reaction mixtures contain a receptor enzyme that is known to be activated or inhibited by a ligand, the ligand itself, at one or more of a plurality of selected concentrations, and either different test compounds being screened for their ability to inhibit or stimulate ligand-receptor binding, and/or different concentrations of such a test compound. After carrying out the individual reactions, the reaction mixtures are combined for separation of and detection of the products and substrates.

In both types of assays, the products and preferably the substrates are separated on a single separation medium, and the separation characteristic of each product and a signal related to the amount of the product are determined. From this, the amount of substrate converted to the corresponding product by each enzyme in the reaction can be determined. A preferred separation characteristic is electrophoretic mobility, where the products and substrates are separated, for example, by capillary electrophoresis (CE). The separation and detection steps are considered in Section C. In another aspect, the invention provides a set of substrates for the multiplexed reaction method, as discussed in Section D.

A. Single-Reaction Format

Multiplexed assays of enzymes and/or enzyme substrates are performed, whereby the enzyme activity of the medium is as to at least one enzyme is determined, particularly the effect of an agent on the enzyme activity of the medium. Families of enzymes sharing a common characteristic, or families of substrates sharing a common functionality acted on by an enzyme, or combinations thereof, are employed in the rapid and efficient evaluation of enzymatic activity of an enzyme composition. The enzymes of the enzyme composition need have no commonality of function, other than being of interest in terms the purpose of the assay, e.g. impact of, for example, a drug in terms of side effects.

The plurality of substrates and/or products is separated and detected, where the presence and amount of individual enzymes can be determined or where specific changes in the amount or nature of the substrates and/or products is indicative of the effect of an agent. Conveniently, the products may be determined individually by capillary electrophoresis, where the amount or nature of the products in the presence of the agent may be compared to the result in the absence of the agent. The subject methodology finds particular use for screening compounds for their effect on enzyme activity, changes in cellular enzyme activity or enzyme activity of a medium of interest.

The assay requires having a set of substrates that can be individually determined. Depending on the nature of the enzyme activity to be determined, each of the substrates will have the appropriate functionality and conformation about the functionality to permit binding to the enzyme active site and undergoing enzymatic modification. The individual substrates are labeled or become labeled as a result of the enzymatic reaction, whereby the enzymatic reaction results in a change in a separation characteristic that allows for separation between the reactant and product. Usually, the changed characteristic will be a change in migration time, such as involved in electrophoresis, chromatography and mass spectrometry. One exemplary separation characteristic is electrophoretic mobility, which will depend on the predominantly on the charge, mass, and shape, i.e., radius, of the molecule, but also on secondary factors, such as shape and hydrophobicity. According to an important feature of the invention, the products produced by enzymatic conversion of the substrates in a set have different separation characteristics from one another and from their corresponding substrates. Preferably, the substrates in the set also have different separation characteristics from one another and from each of the products in the set, such that each substrate and its corresponding product can be uniquely separated and detected in a multiplexed assay. Exemplary sets of substrates for use in the invention will be discussed below.

The enzymes may be divided into different groups based on the nature of the catalyzed reaction. The enzyme groups include, hydrolases, oxidoreductases, lyases, transferases, isomerases and ligases or synthases. Of particular interest are classes of enzymes that have physiological significance. These enzymes include protein kinases, peptidases, esterases, protein phosphatases, isomerases, glycosylases, synthetases, proteases, dehydrogenases, oxidases, reductases, and the like, particularly enzymes involved in making or hydrolyzing esters, both organic and inorganic, glycosylating, and hydrolyzing amides. In any class, there may be further subdivisions, as in the kinases, where the kinase may be specific for phosphorylation of serine, threonine and/or tyrosine residues in peptides and proteins.

The enzyme combinations will include at least 2 enzymes, usually at least 3 enzymes and may include 4 or more enzymes. While any maximum number of enzymes will be arbitrary, as a practical matter, there will usually be fewer than 12 different enzymes, more usually fewer than 9, generally in the range of 2 to 8, more usually in the range of 3 to 6, conveniently 4 to 6. A group of enzymes will generally have compatible reaction conditions, such as pH and ionic strength, however cofactor requirements, metal ion requirements, and the like, involving assay components having relatively low mass concentrations, e.g. cofactors, need not be common.

By independently active is intended that less than about 20% of the conversion of a substrate will be due to enzymes other than the intended enzyme. Common conditions require that each of the enzymes provides a measurable rate during the course of the reaction and will generally be that each of the enzymes has at least about 10%, usually at least about 20%, preferably at least about 50% of its maximum turnover rate for the particular substrate, without significant interference from the components added for the other enzymes.

For each assay determination, the components are combined under appropriate conditions for the enzyme(s) with the appropriate substrates. Depending on the nature of the enzymes and assay, the substrates may be naturally occurring or synthetic, frequently synthetic. Since for the most part, separation techniques are used for detection of the product, the product will be detectable, usually having a label that allows for spectrophotometric, particularly fluorimetric, detection or electrochemical detection.

Illustrative of the subject invention is the exemplification of multiplexed kinase assays. The kinases are a large group of enzymes that phosphorylate a hydroxyl group, many of which have high specificity for a particular environment for the hydroxyl group, may provide intra- or interphosphorylation (one may compete with the intraphosphorylation with a high concentration of a competitive substrate), and employ a common reactant—ATP—and generally have about the same medium requirements. The concentration of enzyme will generally be in the range of about 1 pM to 1 $\mu$M, more properly $10^{-6}$–1 IU/ml (IU is defined as 1 $\mu$mole/min of product formation in optimal conditions). Exemplary assay conditions are given in Examples 1–8.

One may vary the reaction conditions depending on the targeted kinase(s); in vitro conditions to support activity of exemplary kinases are exemplified below and/or otherwise known in the art. For example, the reaction generally requires the presence of an effective amount of a nucleoside triphosphate, such as ATP, usually at a concentration in the range of about 0.1–20 mM. The buffer, such as HEPES or Tris, will generally be at a concentration in the range of about 1–50mM, at a pH in the range of about 5–9. Individual enzymes will generally be present in an amount in the range of about 1 pg–5 ng/$\mu$l. Frequently cations are employed, such as Mg, Mn and Ca, generally at concentrations in the range of about 0.1–5 mM. Other additives may include DTT at a concentration in the range of about 0.1–2 mM. In some instances sodium ortho-vanadate may be employed at a concentration in the range of about 0.5–2 mM to inhibit contaminating phosphatases. Also, inert protein may be included, such as ovalbumin, serum albumin, etc., generally at a concentration in the range of about 0.1–5 mg/ml, to prevent non-specific binding and inactivation of low concentration assay components, especially to prevent enzyme binding to the surface. For many mammalian kinases, the reaction is carried out at room or elevated temperatures, usually in the range of 200 to 40° C., conveniently at room (ca. 25° C.) temperature. For high-throughput applications, reaction time is minimized, and is usually from 0.01 to 4 h, more usually about 0.1 to 1 h.

Generally control measurements will be performed, where the rate of a single enzyme will be determined with a specific substrate, as well as the reaction of the enzyme with combinations of substrates for other enzymes, in the presence or absence of its respective substrate.

In performing evaluations of candidate compound activity, the candidate compound is added at a desired concentration or a plurality of assays may be performed with the candidate compound at different concentrations, covering ranges of 1 to 5 orders of magnitude. Depending on the activity range of interest, the concentration of the candidate may range from about 0.1 pM to 1 mM, depending on the anticipated activity of the candidate, the number of enzymes in the medium, the nature of the indication for which the candidate is being investigated, etc. Of particular interest are candidate compounds, which are being investigated for biological activity, e.g. drugs, usually less than 5 kDa, either naturally occurring or synthetic.

After combining all of the components in the reaction mixture, typically the enzymes and candidate compound will be added first, followed by the simultaneous addition of the substrates, the reaction is allowed to proceed. One or more aliquots may be taken to obtain a time course of the reaction as to each of the substrates. As to each aliquot, the reaction may be quenched by adding an inhibitor, stopped by denaturing processes, such as heating, initiation of separation of the substrate from the enzyme, or other convenient means.

Figure 1B:
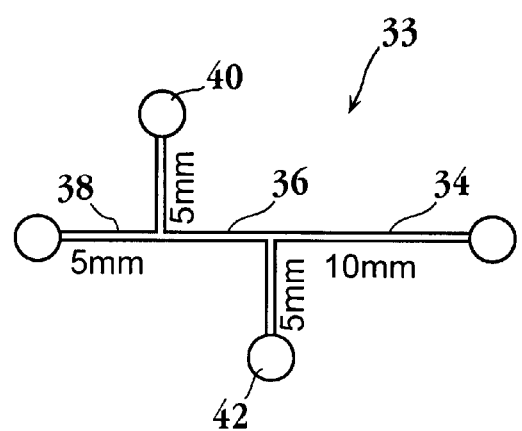

Examples 1–8 below illustrate various embodiments of the assay method in which multiple enzymes are assayed in a single reaction mixture. FIGS. 1A and 1B show the channel network in two types of electrophoretic devices used in carrying out the separation and detection reaction. Briefly, the network in FIG. 1A, indicated 20, includes a separation channel intersected by two side channels, which divide the separation channel into a downstream separation region 24, an intermediate sample volume region 26, and an upstream channel region 28. A sample is contained in reservoir 30 in the network and loaded into region 26. After sample loading, a voltage is placed across the ends of the separation channel, causing electrophoretic migration of the substrate and product components of the reaction to move into and through a separation medium contained in separation region 24. A detector (not shown), such as a standard confocal fluorescence detector, positioned adjacent the downstream end of the region, is used to detect migration of sample substrate and product bands through a detection region, conventionally. Signal intensity of the separated product and substrate bands may be determined, for example, according to measured by peak height or peak area. Details of exemplary run conditions are given in the Examples below.

FIG. 1B shows a microfluidics channel network 33 with a separation channel that is intersected by two side channels, which divide the separation channel into a downstream separation region 34, an intermediate sample volume region 36, and an upstream channel region 38. A sample contained in reservoir 40 in the network is loaded into region 36 by drawing sample from the reservoir into reservoir 42. After sample loading, the sample substrate and product components are separated and detected as above.

Figure 2A:
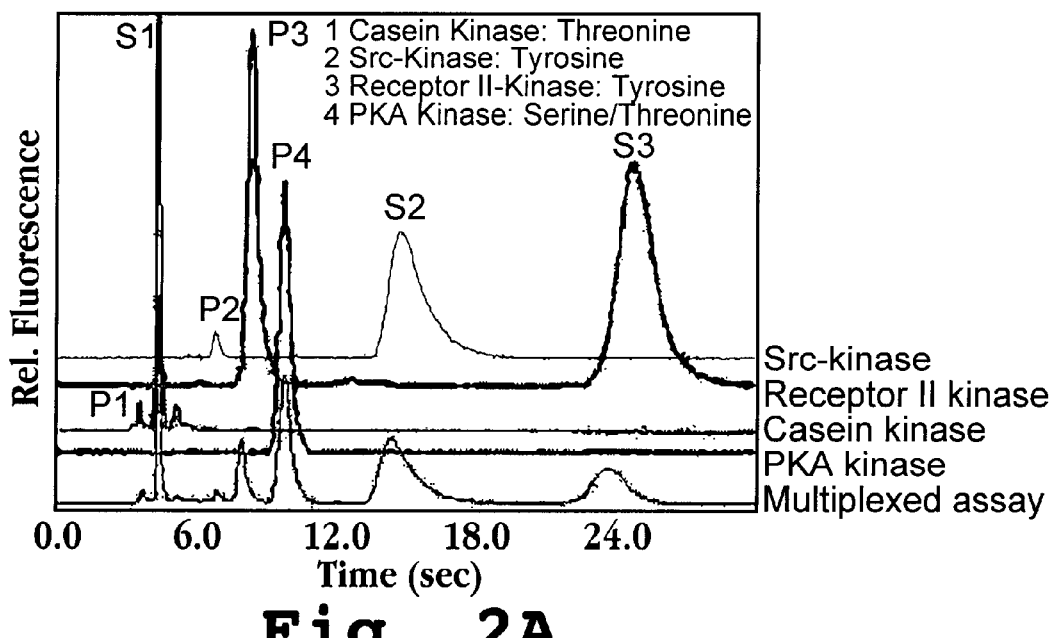
FIGS. 2A and 2B are electropherograms of multiplexed enzyme assays with 4 different kinases, showing assay products and substrates (2A), and substrate specificity (2B)

Example 1 describes a single-mixture multiplexed reaction for four different kinase enzymes, in a reaction mixture containing a set of different enzyme substrates. To confirm the enzymatic reactivity, an individual enzyme assay was also performed for each of the 4 enzymes following the same protocol as for the multiplexed assay by using only one enzyme and its substrate in the assay. The peak identification is shown in FIG. 2A.

Figure 2B:
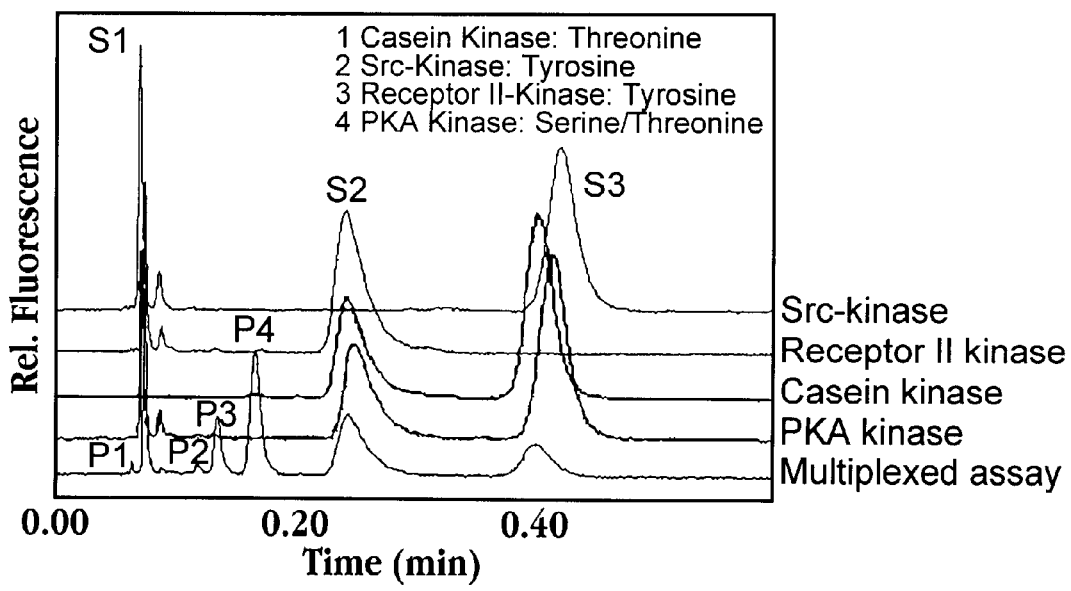

To demonstrate specificity of the multiplexed assay, the assay volume was maintained constant, and the same protocol followed as for the multiplexed assay, except that only one enzyme was added together with the substrates for the other 3 enzymes (i.e., no substrate for the enzyme in the assay mixture). As can be seen in FIG. 2B, there is no cross reactivity between each of the four enzymes and the substrates of the other enzymes used in this experiment.

Figure 3A:
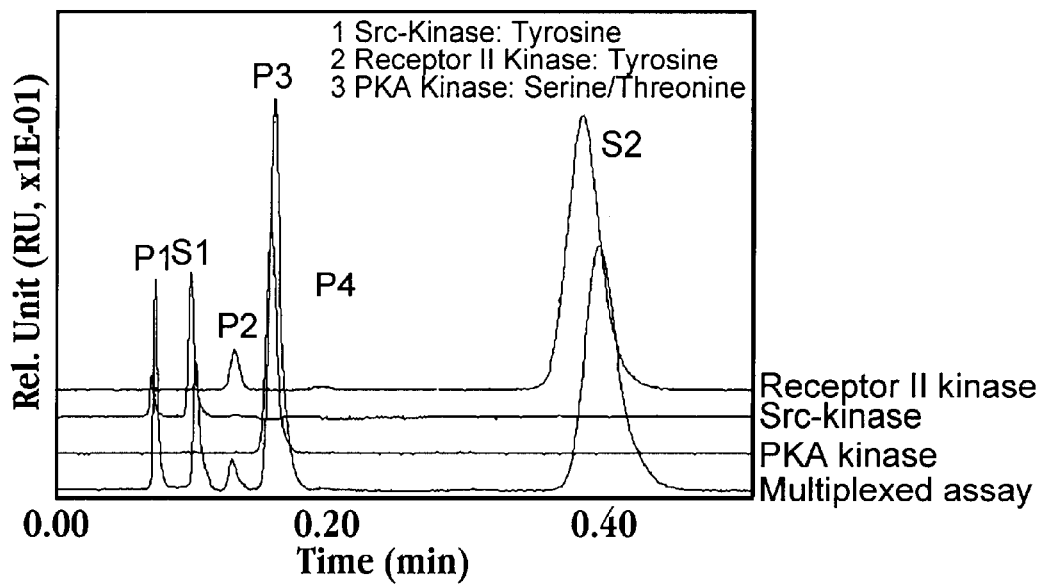
FIGS. 3A and 3B are electropherograms of multiplexed enzyme assays with 4 different kinases, showing assay products and substrates (3A), and substrate specificity (3B)
Figure 3B:
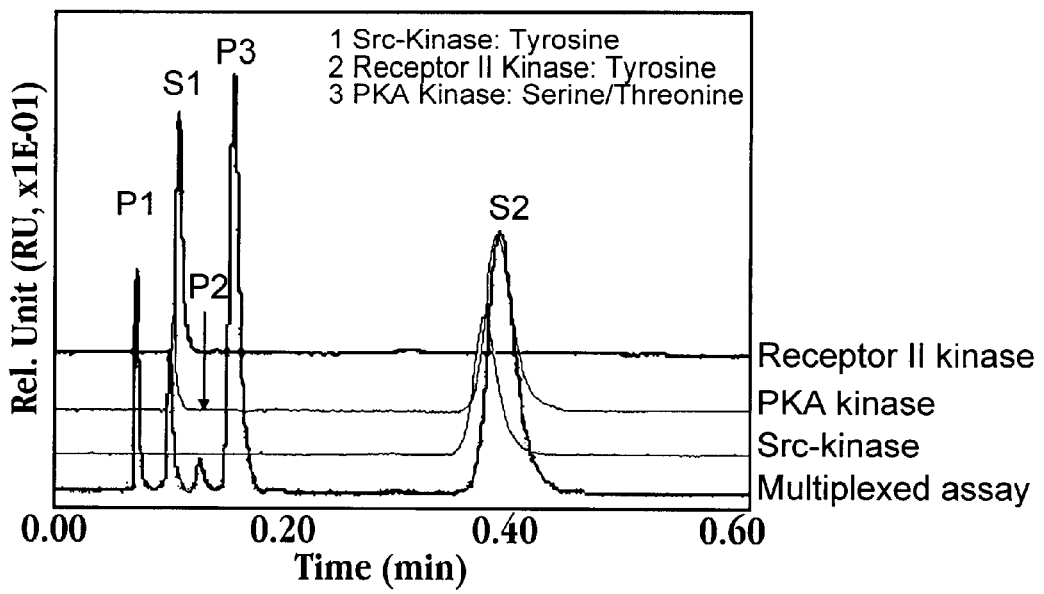

Example 2 describes a similar method involving the three enzymes Src-kinase, Receptor II-kinase and PKA kinase. The purpose of this experiment was to demonstrate multiplexed assay performance after optimizing of the experimental conditions, so as to have balanced amounts of products for the enzymatic reaction, as detailed in the example, and with the results in FIG. 3A. The specificity was also studied for these three enzymes with one enzyme incubating with substrates for the other two enzymes in one tube, as in Example 1, with the results shown in FIG. 3B.

In Example 3, the method is used to assay three classes of kinases: phosphorylate tyrosine, serine and threonine, respectively, with the substrates and reaction conditions given in Example 2. The results, shown in FIG. 4, again demonstrate the ability to detect position and signal intensity for each substrate and corresponding product in the single reaction mixture.

Figure 5A:
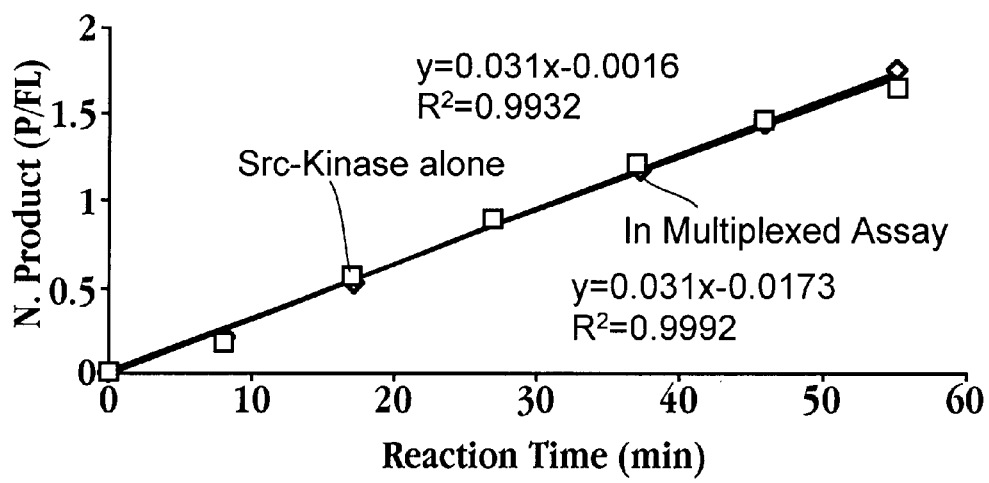
FIGS. 5A and 5B each shows a time course study for enzymes in an individual (5A) and multiplexed (5B) assay format.
Figure 5B:
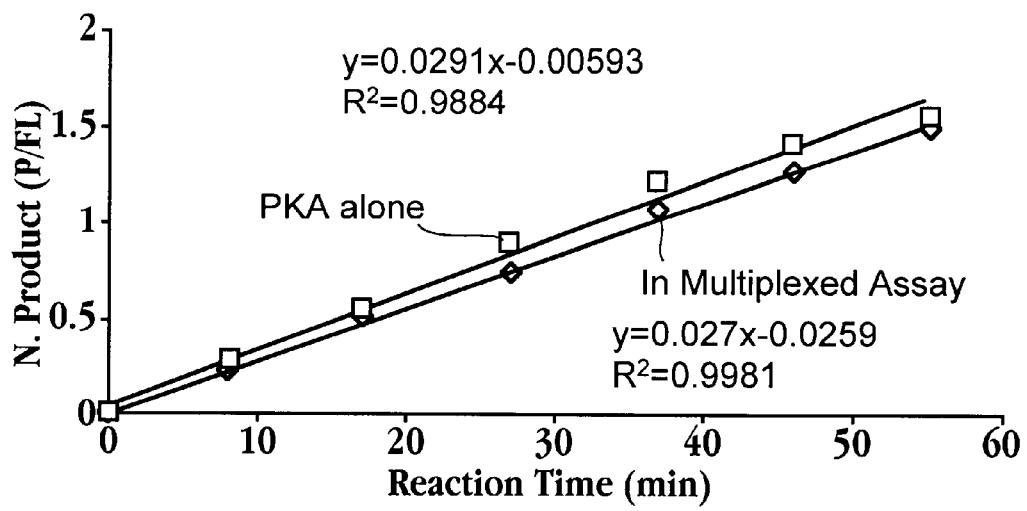

To demonstrate that similar enzyme kinetics are observed in a multi-enzyme assay as in a single-enzyme reaction, a time course for reaction product generated by Src-kinase along or Src-kinase in a multiplexed reaction (FIG. 5A), and for PKA alone and PKA in a multiplexed reaction (FIG. 5B) were carried out. As seen from the product-vs-time plots in the two figures, substantially the same reaction kinetics were observed in both single-enzyme and multiple-enzyme reaction mixtures.

Figure 6A:
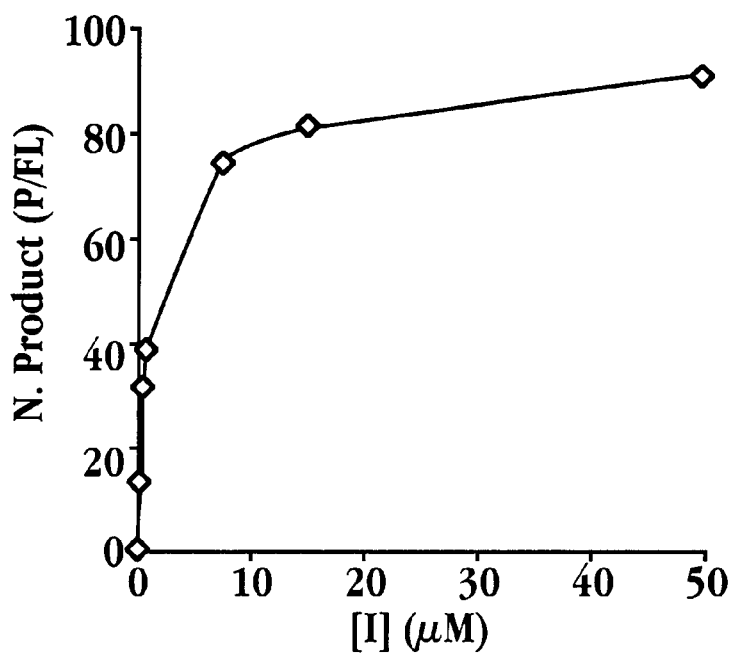
FIGS. 6A and 6B are inhibition measurements in an individual (6A) and multiplexed (6B) assay format.
Figure 6B:
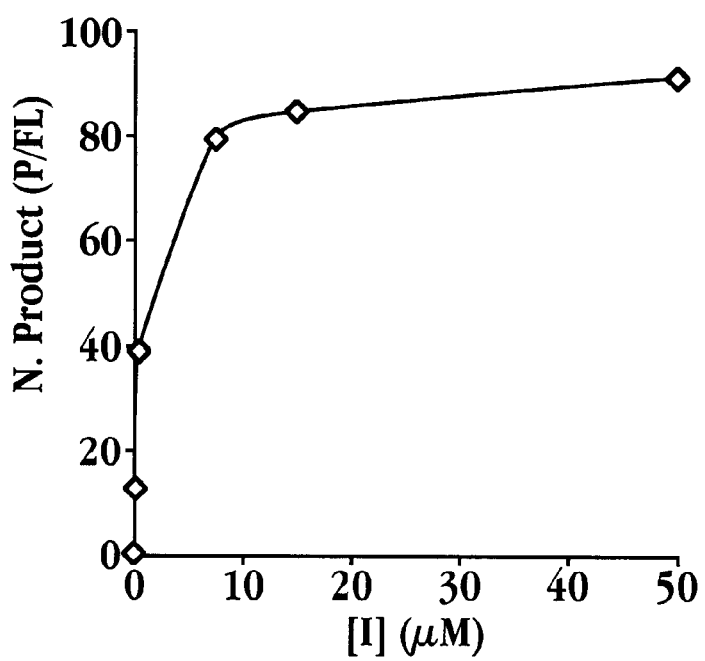

The study reported in Example 5 was designed to show that enzymes in the multiplex-assay format show substantially the same response to enzyme inhibitors as do single enzymes. The enzyme employed was Src-kinase, and a known inhibitor. The enzyme was present either in a single-enzyme format (FIG. 6A), or a multiple-enzyme format (FIG. 6B). As seen from the figures, the presence of additional kinase enzymes in the multiple-enzyme mixture does not affect the inhibition measurement of either kinase. In particular, the $IC_{50}$ values are comparable for the multiplexed assay format and individual assay format. Similar results were also obtained PKA kinase.

Figure 7:
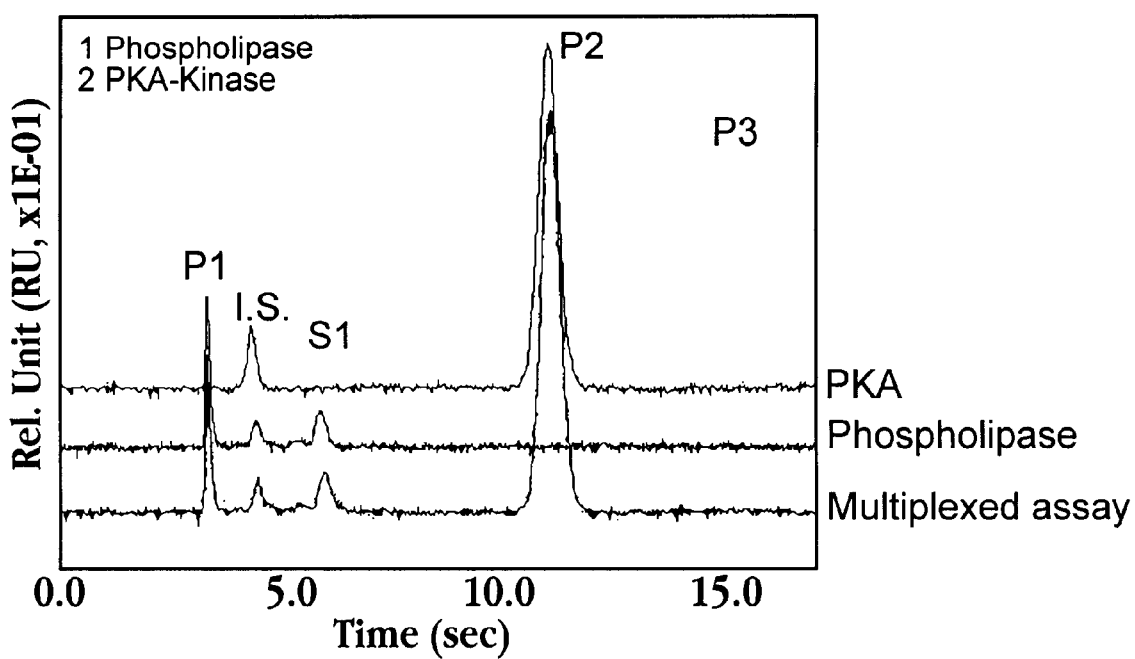
FIG. 7 shows an electropherogram of a multiplexed enzyme assay with phospholipase and PKA kinase.

The assay method described in Example 6 demonstrates that the multiplexed assay is adaptable to different classes of enzymes, where common conditions can be employed to obtain reasonable enzymatic turnover rates. In this example, the two enzymes in the assay are phospholipase and PKA, assayed under the conditions detailed in Example 6. As seen in FIG. 7 the multiplexed assay gives substantially the same assay results as individual phospholipase and PKA assays.

Figure 8:
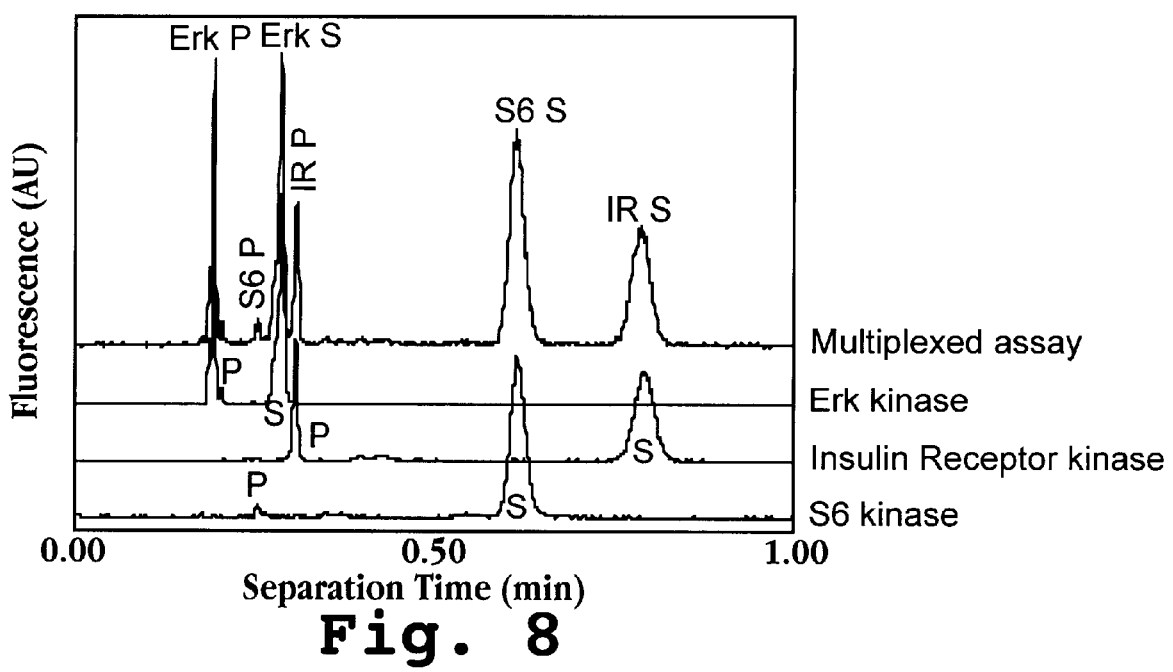
FIG. 8 shows an electropherogram of a multiplexed assay for enzymes in the insulin receptor pathway.

The multiplexed assay method described in Example 7 involves several key enzymes in the insulin-receptor pathway, namely insulin receptor kinase, Erk kinase, and S6 kinase, to demonstrate the use of the assay method is detecting activities of several cellular enzymes in a single pathway, e.g., with coupled function. FIG. 8 shows that the activities of the three enzymes can be simultaneously monitored in a multiplexed assay.

Figure 9A:
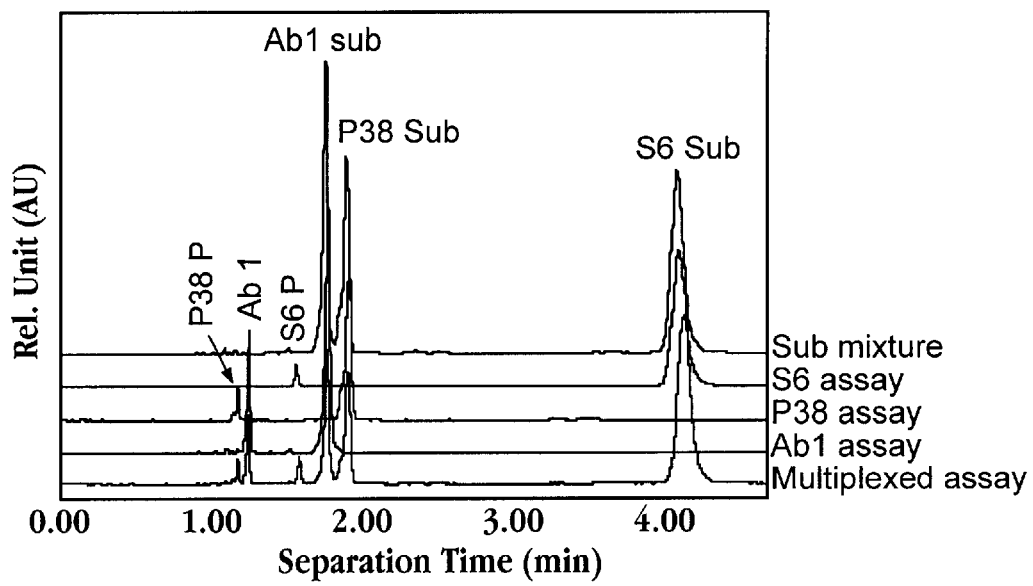
FIGS. 9A and 9B show electropherograms of a multiplexed kinase assay used for monitoring cell signaling pathways.

A similar assay for simultaneously assaying the activities of multiple enzymes in a cell-signaling pathway is given in Example 8, with the kinases S6, P38, and Ab1, with the results shown in FIG. 9A. To investigate specificity, the assay conditions were the same except only one kinase and the substrates for other two kinases were used in the assay to check the cross reactivity. As shown in the FIG. 9B, less than 1% cross reactivity was observed between kinases and the substrates for other kinases. Therefore, these substrates are specific for their respective kinases in this experiment.

It is evident from the above results that multiplexed enzyme assays can be performed, where not only can the activity of the individual enzymes be determined independently of the other enzymes that are present, but also agents may be added and the effect of the agents on each of the enzymes may also be determined. By employing substrates whose mobility shifts after the enzymatic reaction and selecting substrates that can be separated, using for example capillary electrophoresis, the effect of agents on the enzyme activity of members of a class of enzymes can be rapidly determined. In this manner candidate drugs can be rapidly screened for activity, specificity, cross-reactivity and potential side effects in a single vessel and in a single separation.

B. Multiple-Reaction Format

In this general embodiment of the invention, individual enzyme-assay reactions are carried out in separate reaction mixtures. Following enzyme assay, the mixtures (or fractions thereof containing the substrates and products of the reactions) are combined and separated in a single reaction medium, e.g., by CE. Each individual reaction mixture may contain one or more enzymes, and one of more substrates. In its simplest form, a single enzyme to be assayed and a single substrate for that enzyme are preset in each reaction mixture.

The set of substrates employed in the reaction has the same general properties as that required in the single-reaction multiplexed assay. That is, each substrate and the corresponding product have unique separation characteristics, allowing them to be separated from one another. Similarly, all of the products have unique separation characteristics, allowing them to be separated from one another and from all other substrates. As indicated above, the substrates in a set may be distributed among different reaction mixtures, one per mixture, or two or more per mixture.

In one exemplary application, the assay method is applied to ligand-activated or ligand-inhibited receptors, for purposes of screening for and evaluating compounds capable of interfering or activating enzyme activity, by interfering with ligand-receptor interactions. Receptors represent a significant class of targets for drug screening because they are involved in cell growth and metabolism. Of special importance, many receptors are involved in oncogenic processes. Many receptors have enzyme domains, such as the insulin receptor, insulin-like growth factor receptor, epidermal growth factor, and platelet-derived growth factor (White). Some receptors can be coupled to enzyme for assaying the receptors (Bunemann). When a ligand binds to the specific site of a receptor, it typically activates the receptor's enzyme domain. In many cases, the enzyme is a protein kinase, which can be measured by determination of the rate of phosphorylation of a synthetic peptide.

Figure 10:
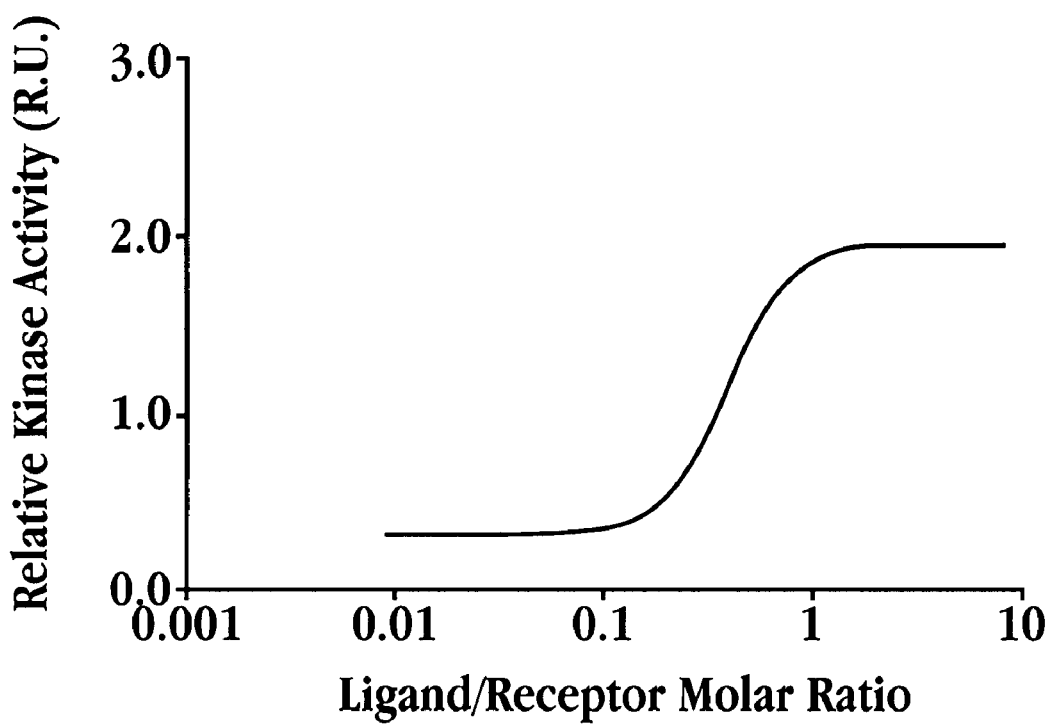
FIG. 10 is a plot showing the level of ligand enhancement of receptor kinase activity.

Since the receptors targeted in this embodiment of the invention either have enzyme domains or can be coupled to an enzyme for assay, the assay method is applicable to screening a library compound for competition with ligand-receptor binding and direct inhibition of the enzyme domain. To illustrate the method, FIG. 10 shows intrinsic and ligand-activity activity levels of epidermal growth factor receptor (EGFR). As seen, the receptor enzyme has intrinsic enzyme activity (low ligand/receptor concentration), which is much lower than the ligand-enhanced receptor enzyme activity. First, if a compound competes with the ligand for binding to the receptor, the receptor enzyme activity would be between stage 2 and stage 1, assuming the compound does not show complete competition. In a second scenario, if the compound is a potent competitor and at very high concentration, the binding equilibrium tilts to compound-receptor, and the receptor enzyme would only show the intrinsic enzyme activity. At the third situation, if the library compound is an inhibitor to the enzyme domain, the receptor enzyme activity will be between 0 and stage 2. A potent inhibitor will totally shut off the enzyme. Based on the above discussion, it is possible to screen a library compound for ligand binding competition and enzyme inhibition. To elucidate the mechanism of changing receptor enzyme activity, a high concentration of the compound can be used. If the enzyme activity never drops below the intrinsic activity, the compound is probably a competitor to the ligand. On the other hand, if the enzyme activity after adding excess amount of a library compound drops below the intrinsic activity or to zero, this compound is most likely an inhibitor to enzyme domain. However, it may not be necessary to do that, since the purpose of finding a compound either competing with ligand or inhibiting enzyme domain is to stop the harmful signal transduction involved in the cellular growth or metabolism (e.g., oncongene process).

In screening for compounds that are capable of inhibiting ligand/receptor binding, there are two, and sometimes three, variables that must be screened, as noted above. The first variable is the test compound itself, e.g., a large number of test compounds derived from a library of potential inhibitors of ligand/receptor interaction. In the present method, a large number of test compounds can be screened in separate assay mixtures, each containing the enzyme and an optimal concentration of ligand, where each reaction mixture contains a substrate from a set of substrates having the same substrate moiety, but different separation characteristics, as detailed in Section D below.

The reactions mixtures, or portions thereof containing the products and substrates, are then combined, separated in a single separation medium, and analyzed as to separation characteristic, e.g., electrophoretic mobility, to identify each product and substrate. Those test compounds that produce a measurable change in product level are identified as potential candidates for drugs capable of interfering with ligand/receptor interaction.

The second variable is test-compound concentration, relative to the concentration of receptor ligand. As noted above, it may be necessary to examine enzyme activity levels at several different ligand/test compound ratios to determine whether the compound is a competitive inhibitor of ligand-receptor binding or is simply inhibiting enzyme activity, and to determine the concentration at which the test compound may be effective. This can be done, in accordance with the invention, by conducting a plurality of separate reactions, each containing the enzyme of interest, an optimal concentration of ligand, each of a plurality of different test compound concentrations, and each of plurality of separate substrates in a substrate set.

The reaction mixtures are then combined and processed as above, to identify each product and substrate. From this information, and the relative levels of product and substrates for each substrate in the set, concentration activity curves can be constructed from a single multiplexed assay result.

The third variable is the effect of the test compound on other enzymes, e.g., other receptor kinases on or in the target cell. As can be appreciated from Section A above, this phase of compound testing can be done efficiently in a multiple-enzyme format, in which the effect of the compound on enzyme-ligand interactions can be assayed in the presence of a plurality of other enzymes, including associated ligands.

Figure 11A:
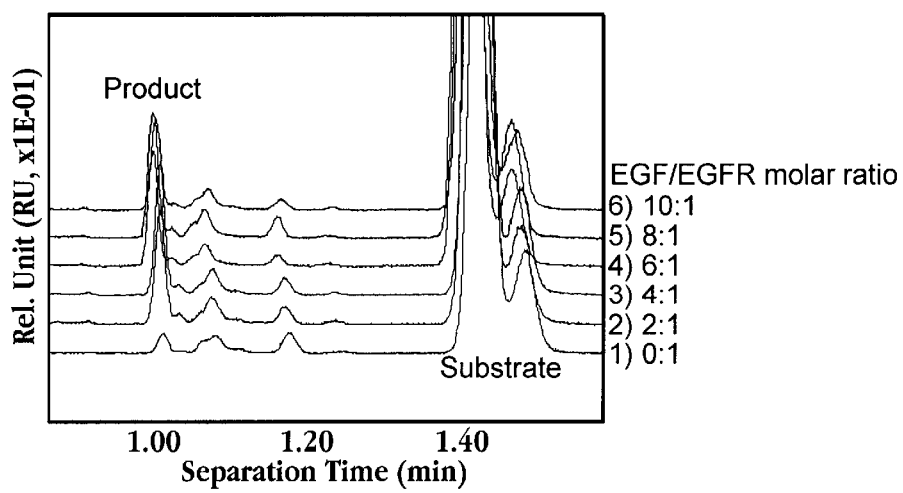
FIGS. 11A and 11B show the effect of various EGF/EGFR ratios on measured levels on EGFR activity with first (11A) and second (11B) substrates.
Figure 11B:
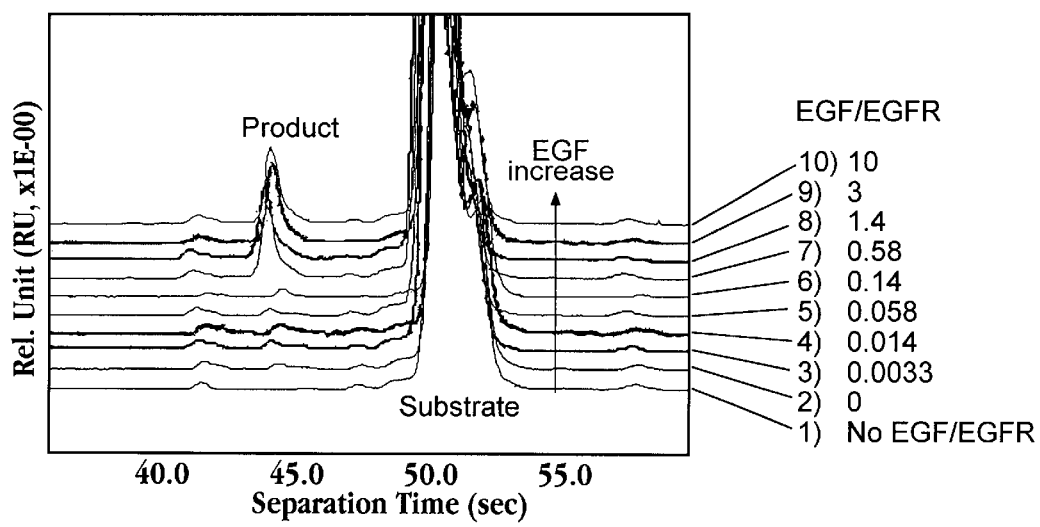
Figure 12A:
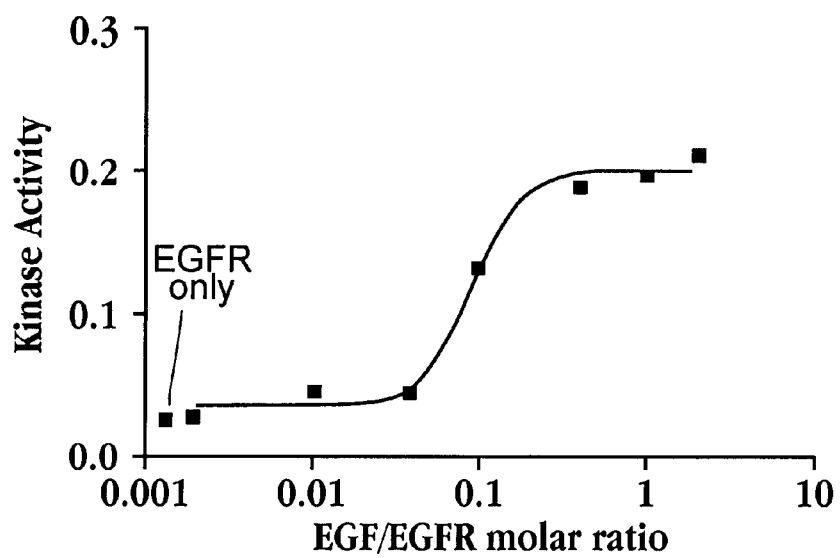
FIGS. 12A and 12B are plots showing the EGF enhancement of EGFR kinase with first (12A) and second (12B) substrates.
Figure 12B:
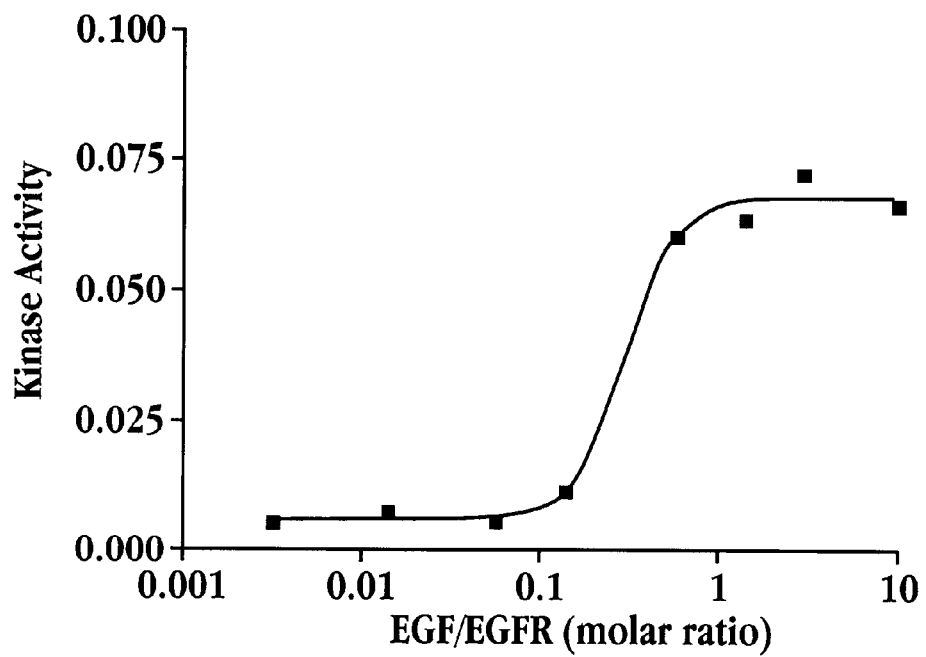

Examples 9–12 below demonstrate the general principles discussed above for a single-assay format. The study in Example 9 is designed to determine optimal ligand/receptor ration for the EGF/EGFR pair, using two different substrates (FIGS. 11A and 11B). The kinase activity measured from FIGS. 11A and 11B were plotted as a function of EGF/EGFR ratios, for both substrates. The plot in FIG. 12A shows a 6.3 fold enhancement in kinase with an optimal EGF/EGFR ratio, when the enzyme is acting on substrate 1. The maximum level of enhancement was about 11-fold with substrate 2, as seen in FIG. 12B.

It can be appreciated how the same information can be obtained in a multiplexed format, in accordance with the invention. Here each different reaction mixture contains one of the selected EGF/EGFR ratios, and one of the substrates from a substrate set. The individual reaction mixtures are then combined, the products and substrates separated in a single separation medium, and the relative levels of substrates and products measured for each reaction. From this, dose response curves like those shown in FIGS. 12A and 12B are constructed.

Example 10 demonstrates the use of the assay to screen for competition (screening antagonists) that can interfere with ligand-activation of a kinase receptor enzyme. In this example, two EGFR fragments were studied for their ability to saturate the binding sites and block binding of EGF and consequent increase in kinase activity when EGF is added. As seen from Table 1 in Example 10, high concentrations of the fragments were able to suppress the enhanced activity of EGFR, but not to basal enzyme levels (activity in the absence of ligand).

To carry out this study in a multiplexed format, the enzyme and ligand, at a fixed ratio, are mixed with each of a plurality of different concentrations of the selected test inhibitor, and one of the substrates from the substrate set. After carrying out each separate reaction, the reaction mixtures are combined and analyzed as above in a single separation medium, yielding a dose response curve for the compound's inhibitory activity.

Figure 13:
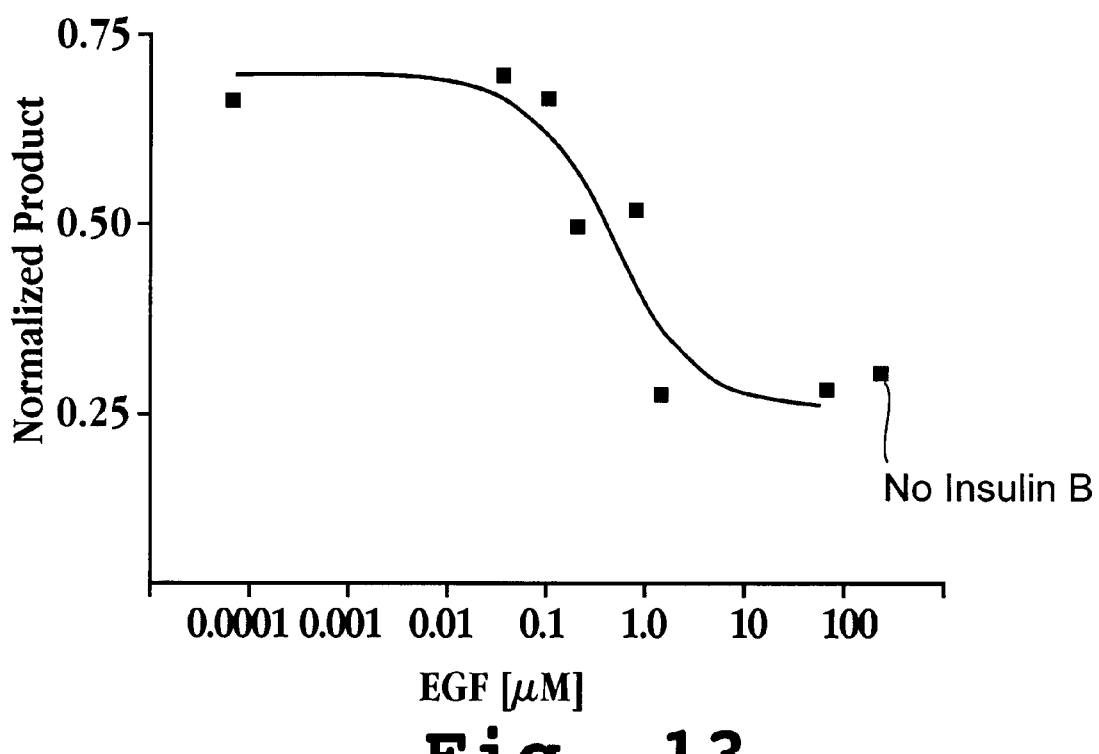
FIG. 13 shows the insulin B dose response in a receptor II kinase assay.

As another example, receptor II (an insulin-related receptor) was studied in connection with insulin-like growth factor (IGF). A significant enhancement (>4 fold) in receptor II kinase activity was observed. Other ligands tested include insulin, insulin α and β chain. Both insulin and insulin β chain stimulated this receptor kinase activity by as much as 20 fold when a high concentration was used (Table 2 in Example 11). One Insulin β chain dose response study for this receptor is shown in FIG. 13. Based on the significant difference of enhancement for this receptor kinase activity from several ligands (4 fold for IGF, >20 fold for Insulin and insulin β chain, only about 3 fold for Insulin α chain), insulin β chain was chosen for demonstrating the receptor-ligand binding assay by monitoring the receptor kinase activity.

Figure 14A:
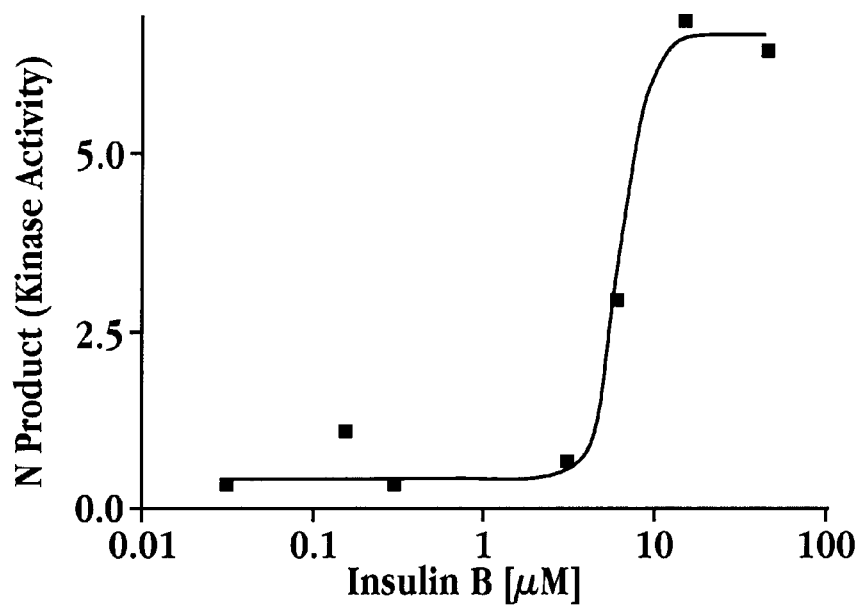
FIGS. 14A and 14B are plots showing changes in receptor II kinase activity at high activating ligand concentration (14A) and low activating ligand concentration (14B) with EGF as competitor.
Figure 14B:
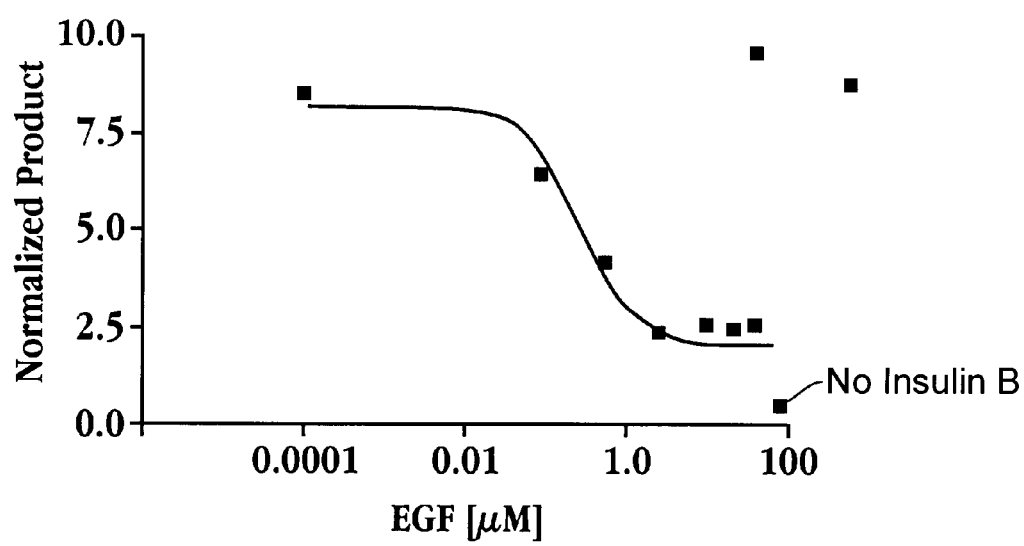

The competition between insulin β chain and epidermal growth factor (EGF) with receptor II receptor was performed to demonstrate the assay method for use in competition between an activating ligand and a putative competitor by monitoring receptor kinase activity. FIG. 14A shows inhibition of ligand-induced receptor II kinase activation by a non-activating ligand, at a high concentration of activating ligand. It is also possible to show near complete competition with EGF when a lower insulin β chain concentration of 3 $\mu$M was used as shown in FIG. 14B.

It will be appreciated from the above how the ligand-inhibition assay just described would be carried out in a multiplexed assay, in accordance with the invention. Each reaction mixture would include the enzyme, an optimally activating (or inhibiting) amount of ligand, each of a plurality of different concentrations of test compound, and a selected substrate from the substrate set. After performing each individual enzyme reactions, the assay mixtures are combined, and the substrates and products separated and quantitated as above. From the information, a dose response curve of the test compound, in its competitive binding to the enzyme, is constructed.

C. Separation and Detection

The products, and preferably the associated substrates, from the assay reactions are separated on a single separation medium or format, meaning that a sample mixture containing the combined products (and preferably all of the substrates) from the reactions is applied to a single separation medium, such as electrophoretic separation medium, a chromatography medium, or a mass spectroscopy medium, and all of the sample product/substrates components are separated on that medium.

A preferred separation medium is an electrophoretic medium, and a suitable separation device is a microfluidics device of the type described above for separating charged components across a separation channel, according to well-known methods. As illustrated in several of the figures, electrophoretic separation and band resolution of a plurality of probes and substrates is readily accomplished by this method.

Conveniently, an aliquot, generally not more than about 5 $\mu$l, is transferred to the sample reservoir of a microfluidics device or capillary electrophoretic device, either directly through electrophoretic or pneumatic injection into an integrated system or by syringe, capillary or the like. Microfluidics devices are described in a number of domestic and foreign Letters Patent and published patent applications. See, for example, U.S. Pat. Nos. 5,750,015; 5,900,130; 6,007,690; and WO 98/45693; WO 99/19717 and WO 99/15876.

FIGS. 1A and 1B illustrate two types of microfluidic devices suitable for use in CE separation and fluorescence detection, as described above. The conditions under which the separation is performed are conventional and will vary with the nature of the products. Longer times will be required for products that have similar mobilities under the conditions of the electrophoresis. The conditions will be applicable to oligopeptides or other substrates using conventional voltages for capillary electrophoresis.

In order to identify each product and substrate, either each substrate and its corresponding reporter must have a detectable reporter that is unique to that product/substrate or, more commonly, to know the relative separation characteristic of each product and substrate, under the selected separation conditions. For example, if the sample is separated by CZE, each product and substrate can be identified from its known or relative migration position with respect to other products and substrates or relative to a detectable internal standard. This is illustrated in several of the figures above, where particular product and substrate bands are identified according to their known migration behavior when applied as a single product/substrate pair on an electrophoretic gel.

Following separation, the components are detected, first to determine a separation characteristic, as above, and secondly, to measure signal intensity, e.g., peak height or peak area, as a measure of the relative amounts of substrate and product for each different substrate in the sample. Assuming that a given substrate and its product both have the same detection characteristics, e.g., fluorescence absorption and emission spectra, the relative amounts of that substrate and product can be determined from their relative peak heights or peaks areas, even if other substrate-product pairs have different detection characteristics. Where product signal alone is measured, it is necessary to know the relative detection characteristics of the various products, to have a standard for comparing their different measured levels.

Methods for measuring product and substrate signals are well known. In one preferred method, the products and substrates are fluorescently labeled. A standard fluorescence-emission source is directed against a detection zone in a downstream portion of the separation medium, and fluorescence emission of the zone is measured by a standard light detector. The signal height or area recorded provides a measure of product and substrate concentration in the sample.

With the above detection information, it is now possible to assign each detected product or substrate-product pair to a particular substrate in the substrate set, and to compare the levels of substrate-to-product conversion for each substrate, corresponding to each different enzyme in a multi-enzyme assay, or each different reaction in a multi-reaction assay.

D. Substrate Set

The substrate set provided by the invention includes a plurality of enzyme substrates, each having (i) an enzyme substrate moiety at which an enzyme in the assay reacts with the substrate, to convert it to the corresponding product, (ii) a mobility modifier that imparts to each substrate and its corresponding product in the set, a unique separation characteristic with respect to the separation characteristics of other substrates and corresponding products in the set, and (iii) a reporter moiety that permits detection of a signal from said substrates and products in the set.

The reporter moiety is any moiety that allows the product and substrate to be detected, preferably quantitatively, following separation in the separation medium. For spectrophotometric detection, fluorophores or dyes may be used. Radiolabeled reporters are another class of suitable reporters. Alternatively, the reporter may be a catalytic moiety that is effective to catalyze a detectable reaction in the presence of suitable reaction components, such as described in co-owned U.S. patent application Serial No. 60/293,821, filed May 26, 2001.

A number of different fluorescers are described in the articles previously noted; namely, Stryer, Science 162, 526 (1968) and Brand, et al, Ann. Rev. Biochem. 41, 843 (1972). One group of fluorescers is the xanthene dyes, which include the fluoresceins derived from 3,6-dihydroxy-9-phenylxanthhydrol and rosamines and rhodamines, derived from 3,6-diamino-9-phenylxanthhydrol. The rhodamines and fluoresceins have a 9-o-carboxyphenyl group, and are derivatives of 9-o-carboxyphenylxanthhydrol. These compounds are commercially available with substituents on the phenyl group, which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-napthhalene sulfonate and 2-p-toluidinyl-6-naphthalene sulfonate. Some naphthalene compounds are found to have some non-specific binding to protein, so that their use requires employing an assay media where the amount of protein is minimized. Other fluorescers are multidentate ligands that include nitrogen-containing macrocycles, which have conjugated ring systems with pi-electrons. These macrocycles may be optionally substituted, including substitution on bridging carbons or on nitrogens. Suitable macrocycles include derivatives of porphyrins, azaporphyrins, corrins, sapphyrins and porphycenes and other like macrocycles, which contain electrons that are extensively delocalized. The azaporphyrin derivatives include phthalocyanine, benzotriazaporphyrin and naphthalocyanine and their derivatives.

In some instances fluorescent fusion proteins may be employed, using green fluorescent protein or other fluorescent protein fused to a polypeptide substrate.

For electrochemical labels, including electrochemiluminescence (ECL), the ECL moieties encompass organometallic compounds that emit electromagnetic radiation, such as visible light, as a result of electrochemical stimulation in accordance with the invention. Examples are 4, 4', 5', 5 tetramethyl bipyridine Re(I)(4-ethyl pyridine)(CO$_3$.$^+$ CF$_3$SO$_3^-$; and Pt(2-(2-thienyl)pyridine)$_2$.

The mobility modifiers in the substrates are selected to impart to the substrate and its corresponding product, a unique separation characteristic with respect to each other and all other substrates and corresponding products in the set. Where the separation characteristic is electrophoretic mobility, the mobility modifier will preferably be selected to impart a unique charge/mass ratio and/or shape to each substrate and product. Where the separation characteristic is chromotographic separation, the different mobility modifiers will have different hydrophobicities, charge, molecular weight, and/or size. For mass spectrometric analysis, the different mobility modifiers will have different masses.

In one general embodiment, the mobility modifiers are unrelated to the substrate, and coupled thereto covalently. Modifiers of this type suitable for imparting different electrophoretic separation characteristics have been detailed in co-owned PCT patent application WO 00/66607, published Nov. 9, 2000, and incorporated herein by reference. Such modifiers typical have repeating subunit groups that impart unique charge/mass ratios to each different modifier.

Where the substrate moiety is a biopolymer, such as an oligopeptide, this moiety itself may be varied to provide differences in separation characteristics, that is, to function as the mobility modifier. For example, amino acids in an oligopeptide that are not related to substrate interaction with the enzyme may be substituted to increase or reduce total molecular weight or size or vary the charge of the oligopeptide. In constructing substrates of this type, one first identifies the amino acids necessary for enzyme specificity, then makes amino acid substitutions, deletions, or additions designed to alter electrophoretic mobility. After constructing a new substrate, it must be tested to confirm that substrate kinetics are unchanged, or if changed, the kinetics must be standardized to a known substrate. A combination of substrate modification and separate mobility modifier may also be employed.

Finally, changes in separation characteristics can be achieved by changes in the mass, charge and/or size of the detection group. Fluorescent groups with different numbers of charged base or acid groups, or different molecular weights are known.

The following examples illustrate various combined-enzyme and single-enzyme assay formats in accordance with the invention. The examples illustrate, but in no way are intended to limit the scope of the invention.

Experimental for Examples 1–8

The instrumentation used comprised a con-focal microscope system equipped with Ar$^+$ laser optical system. A power supply with four independently controlled voltages was used to control the separation process. Two kinds of LabCard™ microfluidic devices were employed as depicted below as stick diagrams for the separations of multiplexed assay mixture (FIG. 1). The channel dimension is 35 µm depth×80 µm width with various lengths. The reservoirs were 2.5 mm in diameter.

All the reagents and assay buffers are listed below:
Enzymes and Substrates:
Src-kinase (Tyr): Optimal sub: FITC[1]-AEEEIYGEFEAKKKK;
CDC-2 sub: FITC-LCKVEKIGEGTTGVYK
Casein Kinase (Ser): FITC-RRRDDDSDDDK
MAP-Kinase (Thr): FITC-PKTP
PKA-Kinase (Ser/Thr): FITC-GRTGRRNSI
Receptor II-Kinase (Tyr): FITC-KKKSPGEYVNIEFG
[1] Fluorescein isothiocyanate was used to attach fluorescein to the terminal amino group.

The substrate stock solutions were prepared in D.I. H$_2$O at 1 mM. The substrate concentration in each assay is described in the assay protocols. All enzymes were purchased from Upstate Biotechnology, except that Receptor II-kinase was a generous gift.

Reaction Buffers and stock solutions:
1. 100 mM HEPES (pH 7.4) with 2 mg/mL Ovalbumin
2. 50 mM HEPES (pH 7.4)
3. 10 µM fluorescein in 50 mM HEPES
4. 100 µM fluorescein in 50 mM HEPES
5. 50 mM DTT in 50 mM HEPES
6. 50 mM Na$_3$ VO$_4$ in 50 mM HEPES
7. 10 mM MgCl$_2$+5 mM MnCl$_2$ in 50 mM HEPES
8. 100 mM Mg-ATP in 50 mM HEPES All the chemicals for preparing the above solutions were purchased from Sigma Chemicals.

The multiplexed assays in Examples 1–9 were performed with several enzymes (typically two to four) in one tube. The assay mixture contains 50 mM HEPES pH 7.4, and 1 mM DTT, 1 mM Na$_3$ VO$_4$, 1 mM Mg-ATP, 4 mM MgCl$_2$, 2 mM MnCl$_2$, and 50 µM peptide substrate each for each enzyme used in the assay. Various amounts of enzymes were used for different experiments as described in the examples.

Two kinds of LabCard microfluidic devices were employed for electrophoretic separation of substrates and products. These are depicted in FIGS. 1A and 1B, as described above. The channel dimension is 35 μm depth×80 μm width with various lengths. The reservoirs were 2.5 mm in diameter. A powerful supply with four independently controlled voltages was used to control the separation process. The instrumentation used for detection was a con-focal microscope system equipped with Ar$^+$ laser optical system. All the reagents and assay buffers are listed below:

EXAMPLE 1

Multiplexed Enzyme Assay with Four Kinases and Assay Specificity (FIG. 2)

The assay protocol is the same as described in the General protocol. The enzymes used in this experiment were 3 μL each of casein kinase, src-kinase, Receptor II-kinase and PKA kinase. The substrate for src-kinase was cdc-2 and the substrates for the other kinases were listed above for the corresponding kinases. The total assay volume is 60 μL and is incubated at room temperature for 45 min. To stop the reaction, 10 μL of 100 mM EDTA was added to the assay mixture. Before performing an analysis, 70 μL D.I. H$_2$O was added into the assay solution for dilution of the analytes and the salt. To confirm the enzymatic reactivity, an individual enzyme assay was also performed for each of the 4 enzymes following the same protocol as for the multiplexed assay by using only one enzyme and its substrate in the assay. The peak identification is shown in FIG. 2a.

To demonstrate specificity of the multiplexed assay, the assay volume was maintained at 60 μL and the same protocol followed as for the multiplexed assay, except that only one enzyme was added together with the substrates for the other 3 enzymes (i.e., no substrate for the enzyme in the assay mixture). As can be seen in FIG. 2b, there is no cross reactivity between each of the four enzymes and the substrates of the other enzymes used in this experiment.

The separation of the assay products was performed on the modified LabCard microfluidic device with the following injection and separation conditions (sample is always in well 4):

Injection: 450 V at well 2 and ground other 3 electrodes for 30 s.

Separation: 0 V at well 1; 400 V at well 2 and 4; 700 V at well 3.

Detection spot: 5 mm

Ex./Em.: 488 nm/520 nm

Separation medium: 25 mM HEPES+1% PEO, pH7.4

EXAMPLE 2

Multiplexed Enzyme Assay with Three Kinases and Their Specificity (FIG. 3)

The assay protocol is the same as in Example 1. The three enzymes used are Src-kinase, Receptor II-kinase and PKA kinase. The purpose of this experiment is to show multiplexed assay performance after optimizing the experimental conditions, so as to have balanced amount of products for the enzymatic reaction. For the src-kinase, the optimal peptide is used for a fast reaction. The enzyme amount used in this experiment was 1 μL of src-kinase, and 5 μL each for PKA kinase and Receptor II kinase. The assay was incubated for 60 min before stopping the reaction by adding 10 μL of 100 mM EDTA. Before analysis on the modified LabCard microfluidic device, the assay sample was diluted with 70 μL of D.I. H$_2$O. The specificity was also studied for these three enzymes with one enzyme incubating with substrates for the other two enzymes in one tube. The same procedure and pretreatment were used to stop the reactions and dilute the assay sample. The analysis conditions are the same as used for Example 1.

EXAMPLE 3

Figure 4:
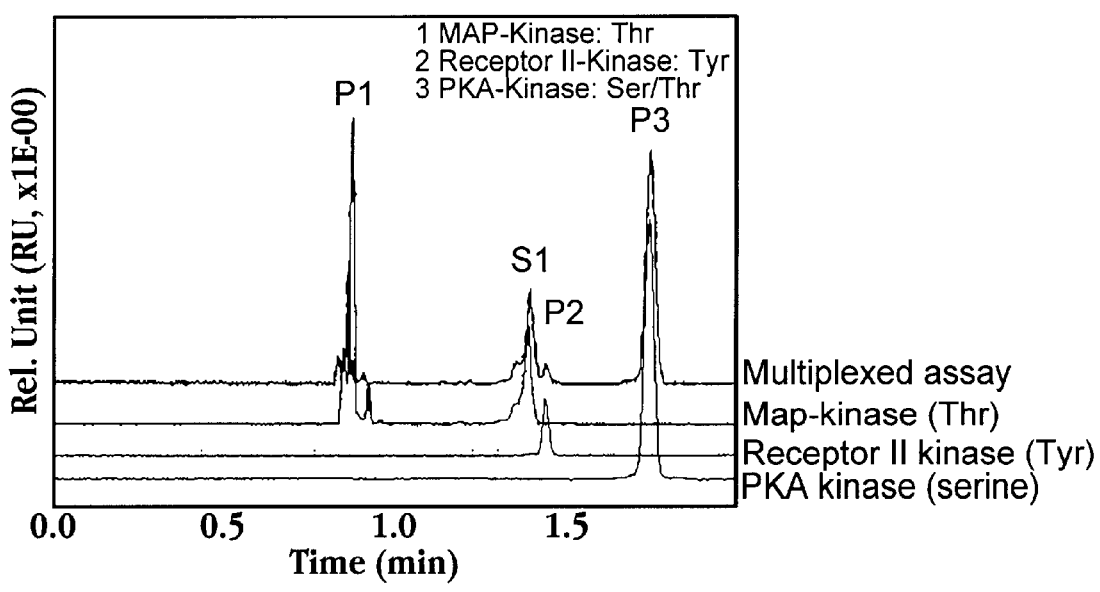
FIG. 4 is an electropherogram for a multiplexed enzyme assay with 3 classes of kinases.

Multiplexed Enzyme Assay with Three Classes of Kinases (FIG. 4)

The assay protocol is the same as used in Example 1. The multiplexed assay is for three classes of kinase, which phosphorylate tyrosine, serine and threonine, respectively. The assay was incubated for 1 hr with 5 μL each for PKA and Receptor II kinase and 3 μL for MAP (Erk-2) kinase. The same procedure as in Example 1 was used to stop the reaction and dilute the assay sample for analysis. The regular LabCard microfluidic device was used for performing the analysis. The injection was done by applying 800 V at well #2 for 60 s while grounding the other 3 wells. The sample is in well #4. The separation condition is: 0 V for well #1, 800 V for wells #2 and #4 and 1500 V for well #3. The separation distance is 3 cm. A relatively long separation distance was required to resolve the components that have similar mobilities.

EXAMPLE 4

Time Course Study (FIG. 5)

The same protocol as used for Example 1 was used for this experiment, except for the enzyme amount and addition of 2 μM fluorescein as an internal standard. Src-kinase and PKA kinase were used for the time course study. Freshly pre-diluted src-kinase (5×) and PKA kinase (4×) in HEPES with 1 mg/mL ovalbumin were used to adjust the final amount of src-kinase to be equivalent to 0.4 μL commercial src-kinase and the final amount of PKA kinase equivalent to 0.5 μL commercial PKA kinase. After adding the enzymes to the assay tube, the reaction was monitored by repeated CE analysis. For either assay with both enzymes or the two separate assays with only one enzyme, equivalent conditions were used except for the presence or absence of enzyme[s]. However, this did not cause any significant difference in reaction volumes, since the volume of the enzyme is less than 1% of the total assay volume. For the multiplexed assay, substrates for both enzymes were present. Only the specific substrate is present for the individual assay. The modified LabCard microfluidic device was used for the analysis with the same conditions as in Example 1. The product peak area normalized to the internal standard (fluorescein) was used to monitor the extent of the reaction. As shown in FIG. 5, both src-kinase and PKA kinase showed very good linearity for about 1 hour in either the multiplexed or individual assays. Also, both enzymes had about the same reactivity in the multiplexed assay vs. individual assays, which indicates that the two enzymes are operating independently in the multiplexed assay at a rate equal to that in the individual assays.

EXAMPLE 5

Inhibition Study (FIG. 6)

This experiment demonstrates that the IC$_{50}$ or inhibition measured in both multiplexed assay format and individual assay format show similar results. The assay conditions were the same as used in Example 1 except for the number of enzymes and use of 1 μM fluorescein as an internal standard. For src-kinase, a known kinase inhibitor provided as a generous gift was used for the inhibition study. A commercially available inhibitor PKI-[6–22] was used for the PKA kinase study. The inhibitor concentration range is 0–50 μM for src-kinase and 0–150 μM for PKA kinase. The reaction was incubated for 40 min with 0.4 μL each of src- and PKA kinase from freshly diluted enzyme solution (similar approach as in Example 4). To stop the reaction for quantifying the inhibition, the assay tubes were heated at >80° C. for 1 min (which denatures the enzymes). If the assay samples were not analyzed immediately, they were stored at −20° C. immediately after enzyme denaturation. The analysis conditions are exactly the same as used in Example 1 with a modified LabCard microfluidic device. The results (FIG. 6) indicate that the presence of the other kinase does not affect the inhibition measurement of either kinase. The $IC_{50}$ values are comparable for the multiplexed assay format and individual assay format.

EXAMPLE 6

Multiplexed Enzyme Assay with PKA Kinase and Phospholipase (FIG. 7)

This experiment demonstrates that it is feasible to perform a multiplexed enzyme assay with different classes of enzymes where common conditions can be employed to obtain reasonable enzymatic turnover rates. The multiplexed assay solution contains 50 mM HEPES, 10 mM $Ca(Ac)_2$, 2 mM $MgCl_2$, 1 mM $MnCl_2$, 2 mM Mg-ATP (Sigma), 3 μM fluorescein as internal standard, 30 μM substrates each for both enzymes, 1 μL of phospholipase (Sigma P7147) and 0.5 μL of PKA kinase. For individual assays, the same conditions as for multiplexed assay were used except that only one enzyme and its substrate were added into the assay mixture. The assays were incubated for 20 min and the enzymes were denatured by heating up to 100° C. for 2 min.

The analysis conditions are the same as used for the modified LabCard microfluidic device, and the separation medium was 25 mM HEPES with 1% PEO. FIG. 7 shows that the assay for these two enzymes can be multiplexed.

EXAMPLE 7

Monitoring an Insulin-stimulated Signaling Pathway (FIG. 8)

Experimental conditions for multiplexing the key enzymes (biochemical samples) involved in the pathway: 50 mM HEPES (pH 7.4), 2 mM $MgCl_2$, 1 mM DTT, 1 mM $Na_3 VO_4$, 1 mM ATP, 30 μM substrates (S6 kinase: FITC-LC-LRRASLG; IR kinase: (5-FAM)-KKKSPGEYVNIEFG; Erk kinase: FITC-LC-PKTP), 3 μL S6 kinase (Upstate biotechnology), 1 μL Erk-2 kinase (Upstate Biotechnology) and 1 μL insulin receptor kinase (Sigma). The assay was incubated for 1.4 hours at room temperature before performing analysis (FIG. 8)

EXAMPLE 8

Figure 9B:
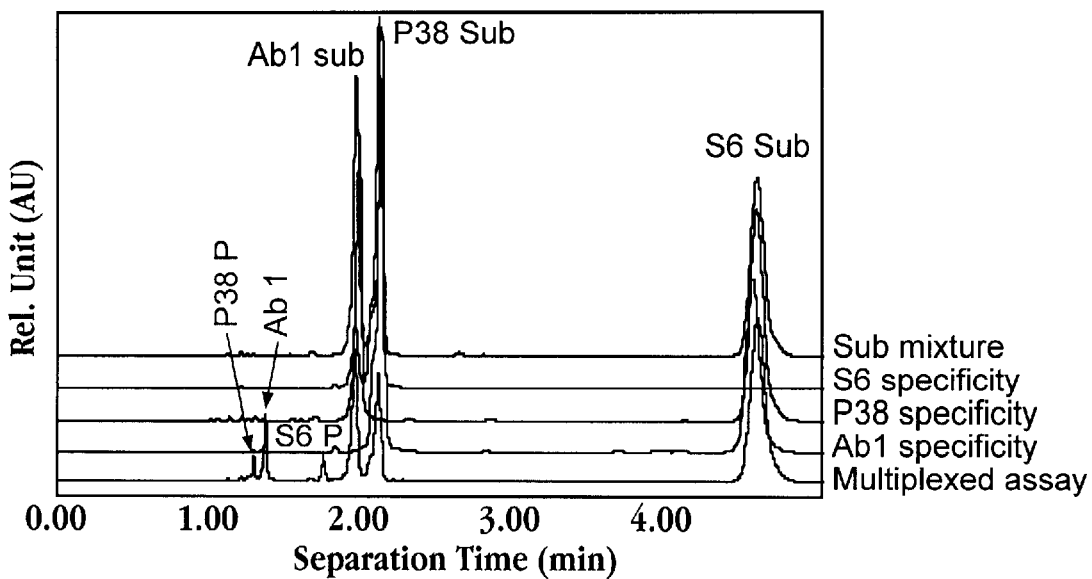

Multiplexed Kinase Assay for Monitoring Cell Signaling Pathways (FIGS. 9A and 9B)

Experimental conditions for multiplexed assay: 50 mM HEPES (pH 7.4), 1 mM DTT, 1 mM $Na_3 VO_4$, 2 mM $MgCl_2$, 2 mM ATP, 60 μM substrates for each kinase (AbI kinase: FITC-LC-EAIYAAPFAK; p38 kinase: FITC-LC-KRELVEPLTPSGEPNQALLR; S6 kinase: FITC-LC-LRRASLG), 3 μL S6 kinase (Upstate biotechnology), 0.5 μL p38 kinase (Upstate biotechnology) and 0.5 μL AbI kinase (CALBIOCHEM). Incubated at room temperature for 3 hrs. To stop the reaction, heat the assay mixture at 80° C. for 1 min to denature the kinases.

Specificity study: the experimental conditions were the same except only one kinase and the substrates for other two kinases were used in the assay to check the cross reactivity. As shown in the Fig., less than 1% cross reactivity was observed between kinases and the substrates for other kinases. Therefore, these substrates are specific for their kinases in this experiment.

| EXPERIMENTAL FOR EXAMPLES 9–12 | |
|---|---|
| MATERIALS: | Stock solutions: |
| | 100 mM HEPES-Na (pH: 7.4) |
| | 1 M NaCl |
| | 50 mM DTT in 50 mM HEPES |
| | 50 mM $Na_3VO_3$ in 50 mM HEPES |
| | 1% Triton X-100 in 50 mM HEPES |
| | 100% glycerol |
| | 100 mM Na-ATP |
| | 10 mM $MgCl_2$ |
| | 5 mM $MnCl_2$ |
| | 1 mM substrate in D.I. $H_2O$ |
| | (Sub1: FITC-RRLIEDAEYAARG; |
| | Sub2: FITC-IEDNEYAREK) |
| | 0.5 mg/mL EGFR kinase (Sigma E-3641) |
| | 0.2 mg/mL EGF in 10% acetic acid |
| | Receptor II kinase (unknown concentration, provided for use as a gift) |
| | 1 mM Receptor II substrate in D.I. $H_2O$ (5-FAM-KKKSPGEYVNIEFG) |
| | 100 μM IGF (prepared in 10% acetic acid, CalBiochem) |
| | 1 mM Insulin β chain (Sigma) |
| Acronyms: | HEPES: N-[2-hydroxyethyl]piperazine-N'-[2-ethanesulfonic acid] |
| | DTT: Dithiothreitol |
| | ATP: Adenosine 5'-triphosphate |
| | EGFR: Epidermal growth factor receptor |
| | EGF: Epidermal growth factor |
| | IGF: Insulin growth factor |
| | Receptor II: an insulin related receptor with a kinase domain |

Protocol for EGFR assay: 25 μL of 100 mM HEPES (pH: 7.4), 10 μL of 10 mM $MgCl_2$+5 mM $MnCl_2$, 3 μL of 1 M NaCl, 1 μL 50 mM DTT, 1 μL 50 mM $Na_3 VO_4$, 3 μL glycerol, 2 μL 1% Triton X-100, 2 μL 100 mM Na-ATP, 3 μL EGFR kinase, various amounts of EGF, and 3 μL substrate (50 μM final concentration) is added to initiate the reaction. Before adding substrate, incubate the mixture for 5 min to activate EGFR by binding to EGF. The incubation was done at 30° C. for 30 min to 1 hr. Either 10 μL of 200 mM EDTA is added or the sample is frozen to stop the kinase reaction before analysis. For the frozen sample, analysis was performed immediately after thawing.

Analysis was done on a LabCard such as, e.g., see FIG. 1B, with 2.5 cm effective separation length. Injection was performed by applying 1000 V at well #2 for 30 s while grounding other wells. The separation conditions are: 0 V for Well #1, 700 V for well #2 and 4, 1500 V for well #3.

Protocol for Receptor II assay: 30 μL of 100 mM HEPES (pH: 7.4), 10 μL of 10 mM $MgCl_2$+5 mM $MnCl_2$, 1 μL 50 mM DTT, 1 μL 50 mM $Na_3 VO_4$, 2 μL 100 mM Na-ATP, 1 μL receptor II kinase, various amounts of Insulin β or other insulin ligands [activating ligand] and/or EGF [competitive inhibitor of activating ligand binding], and last step is to add 3 µL receptor II kinase substrate (50 µM final concentration) to initiate the reaction. Before adding kinase substrate, incubate the mixture for 5 min to activate receptor II kinase by binding to insulin β. The incubation was done at room temperature for 30 min. Either 10 µL of 200 mM EDTA is added or the sample is frozen to stop the reaction before analysis. For the frozen sample, analysis was performed immediately after thawing the samples.

Analysis was done on a modified Henry chip with 5 mm effective separation length. The injection was performed by applying 400 V at well #2 for 45 s while grounding other wells. The separation conditions are: 0 V for Well #1, 400 V for well #2 and 4, 700 V for well #3.

EXAMPLE 9

EGF Enhancement of EGFR Kinase Activity

FIG. 10 shows the EGF enhancement of EGFR kinase activity. The EGF can enhance the EGFR kinase activity by as much as 4 fold as measured with substrate 1 According to the literature, when EGF binds to EGFR, it causes dimerization or internalization of the receptor. However, the mechanism is not well understood. As a transmembrane protein, EGFR has its kinase domain inside the cell. It has been reported that EGF binding to EGFR extracellular receptor domain significantly increases its kinase activity. This process is found in many aspects of the development of carcinomas. The extent of enhancement observed in this study is consistent with what has been reported in the literature.

The dose response of EGFR kinase activity vs. EGF amount was studied with both substrates (FIG. 12A Substrate 1, FIG. 12B substrate 2). For the dose response study, the substrate concentration was 50 µM for either substrate and EGFR concentration was 50 nM. Other conditions are listed in the Experimental section. As would be expected, since EGF binds tightly to EGF, kinase activity enhancement reaches a plateau when a stoichiometric amount of EGF is added. This is reached at a molar ratio of EGF to EGFR equal to 0.5:1 probably because EGF causes dimerization of EGFR so one molecule of EGF can activate two molecules of EGFR.

The kinase activity measured from FIGS. 11A and 11B were plotted as a function of EGF/EGFR ratios, for both substrates. The plot in FIG. 12A shows a 6.3 fold enhancement in kinase with an optimal EGF/EGFR ratio, when the enzyme is acting on substrate 1. The maximum level of enhancement was about 11-fold with substrate 2, as seen in FIG. 12B.

EXAMPLE 10

Screening Assay

This example demonstrates the use of the assay to screen for competition (screening antagonists) that can interfere with ligand-activation of a kinase receptor enzyme. In this example, two EGFR fragments were studied for their ability to saturate the binding sites and block binding of EGF and consequent increase in kinase activity when EGF is added. In this experiment, 50 µM EGFR substrate 2 was used. The EGFR and EGF concentration were used at 50 nM and 55 nM respectively. As listed in Table 1, less enhancement is observed when the fragment concentration was ~10 fold higher than EGF concentration. However, it does not completely suppress the EGF promoted enhancement. The competition phenomenon is demonstrated more clearly with receptor II kinase assay as discussed below.

TABLE 1

Inhibition of EGFR kinase activity from competition of EGFR fragments with EGF

|  | Fragment 661–681/EGF | Fragment 1005–1016/EGF |
| --- | --- | --- |
| Molar ratio | 300 | 300 |
| Inhibition % of Enhanced EGFR* | 22% | 43% |

*Comparing with kinase activity of EGFR saturated with EGF.

EXAMPLE 11

Receptor II Assay by Monitoring Receptor-II Activity

As another example, receptor II (an insulin-related receptor) was studied in connection with insulin-like growth factor (IGF). A significant enhancement (>4 fold) in receptor II kinase activity was observed. Other ligands tested include insulin, insulin α and β chain. Both insulin and insulin β chain stimulated this receptor kinase activity by as much as 20 fold when a high concentration was used (Table 2). One Insulin β chain dose response study for this receptor is shown in FIG. 13. Based on the significant difference of enhancement for this receptor kinase activity from several ligands (4 fold for IGF, >20 fold for Insulin and insulin β chain, only about 3 fold for Insulin α chain), insulin β chain was chosen for demonstrating the receptor-ligand binding assay by monitoring the receptor kinase activity. For this experiment, 25 µM substrate was used with a fixed amount of receptor II and various amounts of ligands to ensure a saturated binding between receptor and ligand.

TABLE 2

Ligand enhancement on receptor II kinase activity in saturating ligand concentrations

| Assay Conditions | Receptor II Kinase Activity Enhancement (fold) |
| --- | --- |
| Receptor II Alone | 1 |
| Receptor 11 + IGF | ~4 |
| Receptor II + Insulin | >20 |
| Receptor II + Insulin α | ~3 |
| Receptor II + Insulin β | >20 |

FIG. 13 shows the activation curve for receptor II kinase by insulin β.

EXAMPLE 12

Screening Assay for Competitive Inhibitors

The competition between insulin β chain and epidermal growth factor (EGF) with this receptor was performed to demonstrate the assay method for use in competition between an activating ligand and a putative competitor by monitoring receptor kinase activity. At a fixed receptor concentration, two concentrations (3 µM and 15 µM) of insulin β chain (activating ligand) were used to conduct the competition experiment with various amounts of EGF (competing non-activating ligand), which led to comparable IC50 of 0.2–0.3 µM. Although the competing, non-activating ligand did not show complete competition at the higher insulin β concentration, it is straightforward to measure the binding competition based on the changes in receptor kinase activity.

FIG. 14A shows Inhibition of ligand-induced receptor II kinase activation by a non-activating ligand, at a high concentration of activating ligand. It is also possible to show near complete competition with EGF when a lower insulin β chain concentration of 3 μM was used as shown in FIG. 14B.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A multiplexed enzyme assay method comprising:

performing a plurality of enzyme reactions with one or more enzymes in the presence of a set of enzyme substrates, under conditions effective to convert an enzyme substrate in the set to a corresponding product in the presence of an enzyme for that substrate, where (i) each enzyme substrate and its corresponding product have different separation characteristics from each other and from the other enzyme substrates in the set and their corresponding products and (ii) each enzyme substrate and its corresponding product have a detection moiety capable of producing a detectable signal, separating the enzyme substrates and products in said reactions in a single separation medium, detecting, for each separated product, a separation characteristic effective to identify that product and a signal related to the amount of the product, and determining, from the detected separation characteristic and signal detected for each product, the amount of enzyme substrate converted to corresponding product in each of said reactions.

2. The method of claim 1, wherein the separation characteristic of said substrates and products is electrophoretic mobility, and said separating includes separating the substrates and corresponding products within an electrophoretic medium, under the influence of an applied electric field.

3. The method of claim 2, wherein the substrates and corresponding products are separated by capillary electrophoresis.

4. The method of claim 1, wherein said detecting further includes detecting, for each of said substrates, a separation characteristic effective to identify that substrate and a signal related to the amount of the substrate.

5. The method of claim 1, wherein said substrates and corresponding products are fluorescently labeled, and said detecting includes detecting the fluorescent signal from each product when irradiated with a fluorescence excitation wavelength.

6. The method of claim 1, wherein said plurality of enzyme reactions are carried out in a single reaction mixture containing a plurality of different enzymes, and each of said enzymes is effective to convert one of said substrates in said reaction mixture to the corresponding product.

7. The method of claim 6, for use in determining the levels of activity of each of a plurality of different enzymes in a cell, under selected cell conditions, wherein said different enzymes in said reaction mixture are obtained from said cell under such selected cell conditions.

8. The method of claim 7, for determining changes in the levels of activity of each of a group of enzymes in a cell, in control and test cell conditions, wherein said performing, separating, detecting, and determining steps are carried out for enzymes obtained from the cells at the control and test conditions.

9. The method of claim 7, for determining changes in the levels of activity of each of a group of enzymes in a cell, when the cell is exposed to an agent known or being tested for its ability to inhibit or activate the level of the activity of one or more of said different enzymes, wherein said performing, separating, detecting, and determining steps are carried out for enzymes obtained from the cells before and after exposure to said agent.

10. The method of claim 9, wherein said group of enzymes are selected from groups consisting of receptor-kinase enzymes and cell-signaling pathway enzymes.

11. The method of claim 1, for assaying the effect of one or more agents in inhibiting or stimulating the activity of a selected enzyme, wherein said performing step includes performing multiple separate enzyme reactions in separate reaction mixtures, where each mixture contains (i) one or more enzymes and (ii) one or more of the substrates from said set, and wherein said performing step further includes combining said reaction mixtures prior to separating the substrates and products of the multiple reactions.

12. The method of claim 11, for use in screening for or evaluating a test compound capable of affecting enzyme activity, wherein the separate reaction mixtures also include one or both of (a) one of a plurality of different test agents being tested for its ability to activate or inhibit the activity of the enzyme, and (b) one of a plurality of different concentrations of a single agent.

13. The method of claim 11, wherein the different substrates in a set include (i) an enzyme substrate moiety, (ii) a mobility modifier that imparts a separation characteristic to each substrate and its corresponding product in the set that is unique with respect to the separation characteristics of other substrates and corresponding products in the set, and (iii) a detection moiety that permits detection of a signal from said substrates and their corresponding products.

14. The method of claim 13, wherein the different substrates in a set have an oligopeptide substrate moiety, and said mobility modifier is selected from the group consisting of (i) non-peptide moieties coupled to the oligopeptide, (ii) one or more amino acid substitutions in said oligopeptide that preserve recognition of said substrate moiety by said enzyme, but alter the separation characteristic of the oligopeptide, and (iii) different reporter moieties with different separation characteristics.

15. The method of claim 11, for assaying interactions between a receptor enzyme and a ligand known to affect the receptor-enzyme activity, wherein said separate enzyme reaction mixtures include (i) said enzyme, (ii) one of the substrates from said set, (iii) one or more different concentrations of said ligand, and wherein in at least one reaction mixture, a concentration of ligand sufficient to produce optimal activation of the enzyme is present.

16. The method of claim 15, wherein at least one of the reaction mixtures contains substantially no ligand, to provide an enzyme activity level of non-activated enzyme.

17. The method of claim 15, wherein at least some of the reaction mixtures contain one or more test agents that interfere with ligand-activated enzyme activity.

18. The method of claim 15, for assaying the effect of one or more test agents to interfere with ligand-activated enzyme activity, where at least some of the reaction mixtures contain an optimal concentration of ligand and one or more different concentrations of at least one test agent.

19. The method of claim 15, wherein said receptor enzyme is a receptor-kinase enzyme effective, in an activated state, to phosphorylate an oligopeptide substrate, and the substrates in said set include said oligopeptide substrate, a mobility modifier is selected from the group consisting of (i) non-peptide moieties coupled to the oligopeptide, (ii) one or more amino acid substitutions in said oligopeptide that preserve recognition of said substrate moiety by said enzyme, but alter the separation characteristic of the oligopeptide, and (iii) different detection moieties with different separation characteristics.

20. The method of claim 19, wherein said receptor enzyme is selected from the group consisting of EGFR, where the ligand is EGF, receptor II kinase, where the ligand is insulin, and ERK and insulin receptor kinase, where the ligand is insulin.

21. The method of claim 11, wherein said enzyme is a kinase.

22. The method of claim 21, wherein said enzyme is selected from the group consisting of ERK kinase, S6 kinase, P38 kinase, and Abl kinase.

23. A composition for use in performing a multiplexed-enzyme assay, comprising
a plurality of enzymes substrates, each having (i) an enzyme substrate moiety at which an enzyme in the assay reacts with the substrate for conversion to a corresponding product, (ii) a mobility modifier that imparts to each substrate and its corresponding product in the set a unique separation characteristic with respect to the separation characteristics of other substrates and corresponding products in the set, and (iii) a detection moiety that permits detection of a signal from said substrates and products in the set.

24. The composition of claim 23, wherein the detection moiety is a fluorescent reporter.

25. The composition of claim 23, for use in a method for assaying one or more enzymes having an oligopeptide substrate, wherein the substrates in a set have an oligopeptide substrate moiety, and said mobility modifier is selected from the group consisting of (i) non-peptide moieties coupled to the oligopeptide, (ii) one or more amino acid substitutions in said oligopeptide that preserve recognition of said substrate moiety by said enzyme, but alter the separation characteristic of the oligopeptide, and (iii) different detection moieties with different separation characteristics.

* * * * *